(12) United States Patent
O'Brien et al.

(10) Patent No.: US 11,666,221 B2
(45) Date of Patent: Jun. 6, 2023

(54) METHOD, SYSTEM AND SPECULUM-FREE OPTICAL PROBE FOR OPTICAL ASSESSMENT OF CERVIX, AND APPLICATIONS OF SAME

(71) Applicant: VANDERBILT UNIVERSITY, Nashville, TN (US)

(72) Inventors: Christine O'Brien, Nashville, TN (US); Katherine Cochran, Nashville, TN (US); Anita Mahadevan-Jansen, Nashville, TN (US); Kristen Rose Findley, Nashville, TN (US); William Stokes, Nashville, TN (US); Lowell Hays, Nashville, TN (US); Mohsin Tejani, Nashville, TN (US); Anne-Marie Crowe, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 770 days.

(21) Appl. No.: 16/613,445

(22) PCT Filed: May 18, 2018

(86) PCT No.: PCT/US2018/033381
§ 371 (c)(1),
(2) Date: Nov. 14, 2019

(87) PCT Pub. No.: WO2018/213698
PCT Pub. Date: Nov. 22, 2018

(65) Prior Publication Data
US 2021/0161388 A1    Jun. 3, 2021

Related U.S. Application Data

(60) Provisional application No. 62/508,049, filed on May 18, 2017.

(51) Int. Cl.
*G01J 3/44* (2006.01)
*A61B 5/00* (2006.01)
(Continued)

(52) U.S. Cl.
CPC ............ *A61B 5/0075* (2013.01); *A61B 5/435* (2013.01); *A61B 5/6875* (2013.01); *G01J 3/0248* (2013.01); *G01J 3/2823* (2013.01)

(58) Field of Classification Search
CPC ..... A61B 5/0075; A61B 5/435; A61B 5/6875; A61B 2562/0233; A61B 5/0086;
(Continued)

(56) References Cited

U.S. PATENT DOCUMENTS 5,450,857 A * 9/1995 Garfield ............... A61B 5/0075
600/587
5,800,350 A * 9/1998 Coppleson ........... A61B 5/0538
600/382

(Continued)

FOREIGN PATENT DOCUMENTS

CN     101146823 A *  3/2008  ............. A61P 31/20

OTHER PUBLICATIONS

Mahadevan-Jansen A, Richards-Kortum RR. Raman spectroscopy for the detection of cancers and precancers. Journal of Biomedical Optics. 1996;1(1):31-70.
(Continued)

*Primary Examiner* — Abdullahi Nur
(74) *Attorney, Agent, or Firm* — Locke Lord LLP; Tim Tingkang Xia, Esq.

(57) ABSTRACT

A method for identification of biochemical markers associated with cervical remodeling over the course of pregnancy of humans includes obtaining Raman signals from the cervix of each of a group of humans with pregnancy at each phase of pregnancy; finding Raman signatures corresponding to
(Continued)

each type of cervical tissue from the obtained Raman signals; and identifying biochemical markers associated with cervical remodeling at each phase of pregnancy corresponding to the Raman signatures.

43 Claims, 13 Drawing Sheets

(51) Int. Cl.
*G01J 3/02* (2006.01)
*G01J 3/28* (2006.01)
(58) Field of Classification Search
CPC .............. A61B 5/14507; A61B 5/14546; G01J 3/0248; G01J 3/2823; G01J 3/44; G01N 21/65; G01N 2201/084
See application file for complete search history.

(56) References Cited

U.S. PATENT DOCUMENTS

| | | | | |
|---|---|---|---|---|
| 8,326,404 | B2* | 12/2012 | Zeng | G01N 21/6486 600/475 |
| 2003/0191398 | A1 | 10/2003 | Motz et al. | |
| 2007/0038123 | A1 | 2/2007 | Fulghum | |
| 2013/0222799 | A1* | 8/2013 | Ashok | G01N 21/645 356/301 |
| 2014/0343384 | A1 | 11/2014 | Floyd et al. | |
| 2017/0050043 | A1 | 2/2017 | Kang et al. | |
| 2017/0224220 | A1* | 8/2017 | Tunnell | G01J 3/02 |

OTHER PUBLICATIONS

Kanter EM, Majumder S, Vargis E, Robichaux-Viehoever A, Kanter GJ, Shappell H, Jones Iii HW, Mahadevan-Jansen A. Multiclass discrimination of cervical precancers using Raman spectroscopy. Journal of Raman Spectroscopy. 2009;40(2):205-11. doi: 10.1002/jrs.2108.
Kanter EM, Vargis E, Majumder S, Keller MD, Woeste E, Rao GG, Mahadevan-Jansen A. Application of Raman spectroscopy for cervical dysplasia diagnosis. Journal of Biophotonics. 2009;2(1-2):81-90. doi: 10.1002/bio.200910001.
Vargis E, Byrd T, Logan Q, Khabele D, Mahadevan-Jansen A. Sensitivity of Raman spectroscopy to normal patient variability. Journal of Biomedical Optics. 2011;16(11):117004-. doi: 10.1117/1.3646210.
Vargis E, Brown N, Williams K, Al-Hendy A, Paria B, Reese J, Mahadevan-Jansen A. Detecting Biochemical Changes in the Rodent Cervix During Pregnancy Using Raman Spectroscopy. Annals of Biomedical Engineering. 2012;40 (8):1814-24. doi: 10.1007/s10439-012-0541-4.
Lieber CA, Mahadevan-Jansen A. Automated method for subtraction of fluorescence from biological Raman spectra. Appl Spectrosc. 2003;57(11):1363-7. Epub Dec. 9, 2003. PubMed PMID: 14658149.
Vargis E, Byrd T, Logan Q, Khabele D, Mahadevan-Jansen A. Sensitivity of Raman spectroscopy to normal patient variability. Journal of Biomedical Optics. 2011;16(11):117004-1170049.
Holt R, Timmons BC, Akgul Y, Akins ML, Mahendroo M. The molecular mechanisms of cervical ripening differ between term and preterm birth. Endocrinology. 2011;152(3):1036-46.
Blencowe H, Cousens S, Chou D, Oestergaard M, Say L, Moller A-B, Kinney M, Lawn J. Born Too Soon: The global epidemiology of 15 million preterm births. Reproductive Health. 2013;10(Suppl 1):1. PubMed PMID: 1463933756; 18811758.
Behrman RE, Butler AS. Preterm birth: causes, consequences, and prevention: National Academies Press; 2006.
Menon R. Spontaneous preterm birth, a clinical dilemma: etiologic, pathophysiologic and genetic heterogeneities and racial disparity.

Acta Obstet Gynecol Scand. 2008;87(6):590-600. Epub Jun. 24, 2008. doi 10.1080/00016340802005126. PubMed PMID: 18568457.
Ruiz RJ, Fullerton J, Dudley DJ. The interrelationship of maternal stress, endocrine factors and inflammation on gestational length. Obstetrical & gynecological survey 2003;58(6):415-28.
Robinson JN, Regan JA, Norwitz ER, editors. The epidemiology of preterm labor. Seminars in Perinatology; 2001: Elsevier.
Macdonald PC, Gant NF, Leveno KJ, Gilstrap LC, Hankins G, Clark SL. Williams Obstetrics 20th Edition: Appleton & Lange; 1996.
Hacker NF, Gambone JC, Hobel CJ. Hacker & Moore's Essentials of Obstetrics and Gynecology: Saunders; 2009.
Iams JD. Prediction and early detection of preterm labor. Obstet Gynecol. 2003;101(2):402-12. PubMed PMID: 12576267.
Catalano PM, Ashikaga T, Mann LI. Cervical change and uterine activity as predictors of preterm delivery. American joumal of perinatology. 1989;6(02):185-90.
Lee HJ, Park TC, Norwitz ER. Management of pregnancies with cervical shortening: a very short cervix is a very big problem. Reviews in Obstetrics and Gynecology. 2009;2(2):107.
Moroz LA, Simhan HN. Rate of sonographic cervical shortening and the risk of spontaneous preterm birth. American Journal of Obstetrics and Gynecology. 2012;206(3):234. e1-. e5.
Okitsu O, Mimura T, Nakayama T, Aono T. Early prediction of preterm delivery by transvaginal ultrasonography. Ultrasound in Obstetrics & Gynecology. 1992;2(6):402-9.
Ludmir J, Sehdev HM. Anatomy and physiology of the uterine cervix. Clinical Obstetrics and Gynecology. 2000;43 (3):433-9. Epub Aug. 19, 2000. PubMed PMID: 10949747.
Aspden RM. Collagen organisation in the cervix and its relation to mechanical function. Coll Relat Res. 1988;8 (2):103-12. PubMed PMID: 3378391.
Word RA, Li X-H, Hnat M, Carrick K, editors. Dynamics of cervical remodeling during pregnancy and parturition: mechanisms and current concepts. Seminars in reproductive medicine; 2007.
Leppert PC. Anatomy and physiology of cervical ripening. Clinical Obstetrics and Gynecology. 1995;38(2):267-79.
Osmers R, Rath W, Adelmann-Grill B, Fittkow C, Kuloczik M, Szeverenyi M, Tschesche H, Kuhn W. Origin of cervical collagenase during parturition. American Journal of Obstetrics and Gynecology. 1992;166(5):1455-60.
Myers KM, Paskaleva A, House M, Socrate S. Mechanical and biochemical properties of human cervical tissue. Acta Biomaterialia. 2008;4(1):104-16.
House M, Kaplan DL, Socrate S. Relationships Between Mechanical Properties and Extracellular Matrix Constituents of the Cervical Stroma During Pregnancy. Seminars in Perinatology. 2009;33(5):300-7. doi: 10.1053/j.Semperi.2009.06.002.
Akins ML, Luby-Phelps K, Bank RA, Mahendroo M. Cervical softening during pregnancy: regulated changes in collagen crosslinking and composition of matricellular proteins in the mouse. Biology of Reproduction. 2011;84 (5):1053-62.
Rechberger T, Uldbjerg N, Oxlund H. Connective tissue changes in the cervix during normal pregnancy and pregnancy complicated by cervical incompetence. Obstet Gynecol. 1988;71(4):563-7. Epub Apr. 1, 1988. PubMed PMID: 3353047.
Myers KM, Socrate S, Paskaleva A, House M. A study of the anisotropy and tension/compression behavior of human cervical tissue. Journal of Biomechanical Engineering. 2010;132(2):021003-.
Myers K, Socrate S, Tzeranis D, House M. Changes in the biochemical constituents and morphologic appearance of the human cervical stroma during pregnancy. European Journal of Obstetrics & Gynecology and Reproductive Biology. 2009;144:S82-S9.
Feltovich H, Hall TJ, Berghella V. Beyond cervical length: emerging technologies for assessing the pregnant cervix. American Journal of Obstetrics and Gynecology. 2012;207(5):345-54.
Jokhi R, Brown B, Anumba D. The role of cervical Electrical Impedance Spectroscopy in the prediction of the course and outcome of induced labour. BMC Pregnancy and Childbirth. 2009;9(1):40.
McFarlin B, Bigelow T, Laybed Y, O'Brien W, Oelze M, Abramowicz J. Ultrasonic attenuation estimation of the pregnant cervix: a preliminary report. Ultrasound in Obstetrics & Gynecology. 2010;36(2):218-25.

(56) References Cited

OTHER PUBLICATIONS

Feltovich H, Nam K, Hall TJ. Quantitative ultrasound assessment of cervical microstructure. Ultrasonic Imaging. 2010;32(3):131-42.
Swiatkowska-Freund M, Preis K. Elastography of the uterine cervix: implications for success of induction of labor. Ultrasound in Obstetrics & Gynecology. 2011;38(1):52-6.
Badir S, Mazza E, Zimmermann R, Bajka M. Cervical softening occurs early in pregnancy: characterization of cervical stiffness in 100 healthy women using the aspiration technique. Prenatal diagnosis. 2013:1-6.
Anthony GS, Walker RG, Robins JB, Cameron AD, Calder AA. Management of cervical weakness based on the measurement of cervical resistance index. European Journal of Obstetrics & Gynecology and Reproductive Biology. 2007;134(2):174-8.
Myers K, Ateshian GA. Interstitial growth and remodeling of biological tissues: Tissue composition as state variables. Journal of the mechanical behavior of biomedical materials. 2013.
Maul H, Saade G, Garfield RE. Prediction of term and preterm parturition and treatment monitoring by measurement of cervical cross-linked collagen using light-induced fluorescence. Acta Obstetricia et Gynecologica Scandinavica. 2005;84(6):534-6. doi: 10.1111/j.0001-6349.2005.00806.x.
Maul H, Olson G, Fittkow CT, Saade GR, Garfield RE. Cervical light-induced fluorescence in humans decreases throughout gestation and before delivery: preliminary observations. American Journal of Obstetrics and Gynecology. 2003;188(2):537-41.
Schlembach D, MacKay L, Shi L, Maner WL, Garfield RE, Maul H. Cervical ripening and insufficiency: From biochemical and molecular studies to in vivo clinical examination. European Journal of Obstetrics & Gynecology and Reproductive Biology. 2009;144, Supplement 1(0):S70-S6. doi: 10.1016/j.ejogrb.2009.02.036.
Zhang Y, Akins ML, Murari K, Xi J, Li MJ, Luby-Phelps K, Mahendroo M, Li X. A compact fiber-optic SHG scanning endomicroscope and its application to visualize cervical remodeling during pregnancy. Proceedings of the National Academy of Sciences. 2012;109(32):12878-83.
Reusch LM, Feltovich H, Carlson LC, Hall G, Campagnola PJ, Eliceiri KW, Hall TJ. Nonlinear optical microscopy and ultrasound imaging of human cervical structure. Journal of Biomedical Optics. 2013;18(3):031110.
Baños A, Wolf M, Grawe C, Stahel M, Haensse D, Fink D, Hornung R. Frequency domain near-infrared spectroscopy of the uterine cervix during cervical ripening. Lasers in Surgery and Medicine. 2007;39(8):641-6.
Hornung R, Spichtig S, Banos A, Stahel M, Zimmermann R, Wolf M. Frequency-domain near-infrared spectroscopy of the uterine cervix during regular pregnancies.
Robichaux-Viehoever A, Kanter E, Shappell H, Billheimer D, Jones III H, Mahadevan-Jansen A. Characterization of Raman Spectra Measured<i> in Vivo</i> for the Detection of Cervical Dysplasia. Applied Spectroscopy. 2007;61 (9):986-93.
Crow P, Molckovsky A, Stone N, Uff J, Wilson B, Wongkeesong L-M. Assessment of fiberoptic near-infrared Raman spectroscopy for diagnosis of bladder and prostate cancer Urology 2005;65(6):1126-30.
Grimbergen M, van Swol C, van Moorselaar R, Uff J, Mahadevan-Jansen A, Stone N. Raman spectroscopy of bladder tissue in the presence of 5-aminolevulinic acid. Journal of Photochemistry and Photobiology B: Biology. 2009;95 (3):170-6.
Barr H, Kendall C, Bazant-Hegemark F, Moayyedi P, Shetty G, Stone N. Endoscopic Screening and Surveillance for Barrett's Esophagus—Clinical Implications. Medscape General Medicine 2006;8(2):88.
Shetty G, Kendall C, Shepherd N, Stone N, Barr H. Raman spectroscopy: elucidation of biochemical changes in carcinogenesis of oesophagus. British journal of cancer. 2006;94(10):1460-4.
Chrit L, Bastien P, Sockalingum G, Batisse D, Leroy F, Manfait M, Hadjur C. An in vivo randomized study of human skin moisturization by a new confocal Raman fiber-optic microprobe: assessment of a glycerol-based hydration cream. Skin pharmacology and physiology. 2006;19(4):207-15.
Sigurdsson S, Philipsen PA, Hansen LK, Larsen J, Gniadecka M, Wulf H-C. Detection of skin cancer by classification of Raman spectra Biomedical Engineering, IEEE Transactions on. 2004;51(10):1784-93.
Haka AS, Shafer-Peltier KE, Fitzmaurice M, Crowe J, Dasari RR, Feld MS. Diagnosing breast cancer by using Raman spectroscopy. Proceedings of the National Academy of Sciences of the United States of America. 2005; 102 (35):12371-6.
Bergholt MS, Zheng W, Lin K, Ho KY, Teh M, Yeoh KG, So JBY, Huang Z. Characterizing variability in in vivo Raman spectra of different anatomical locations in the upper gastrointestinal tract toward cancer detection. Journal of Biomedical Optics. 2011;16(3):037003-10.
Kanter EM, Majumder S, Kanter GJ, Woeste EM, Mahadevan-Jansen A. Effect of hormonal variation on Raman spectra for cervical disease detection. American Journal of Obstetrics and Gynecology. 2009;200(5):512.e1-.e5.
Morris MD, Mandair GS. Raman assessment of bone quality. Clinical Orthopaedics and Related Research®. 2011;469:2160-9.
Mahadevan-Jansen A, Mitchell MF, Ramanujam N, Utzinger U, Richards-Kortum R. Development of a Fiberoptic Probe to Measure NIR Raman Spectra of Cervical Tissue In Vivo. Photochemistry and Photobiology. 1998,68 (3):427-31. doi: 10.1111/j.1751-1097.1998.tb09703.x.
O'Brien, Christine M. et al., "Characterization of human cervical remodeling throughout pregnancy using in vivo Raman spectroscopy", Proc. of SPIE, 2015, vol. 9303 93032F-3.
Korean Intellectual Property Office (ISR/KR), "International Search Report for PCT/US2018/033381", Korea, dated Nov. 2, 2018.

* cited by examiner

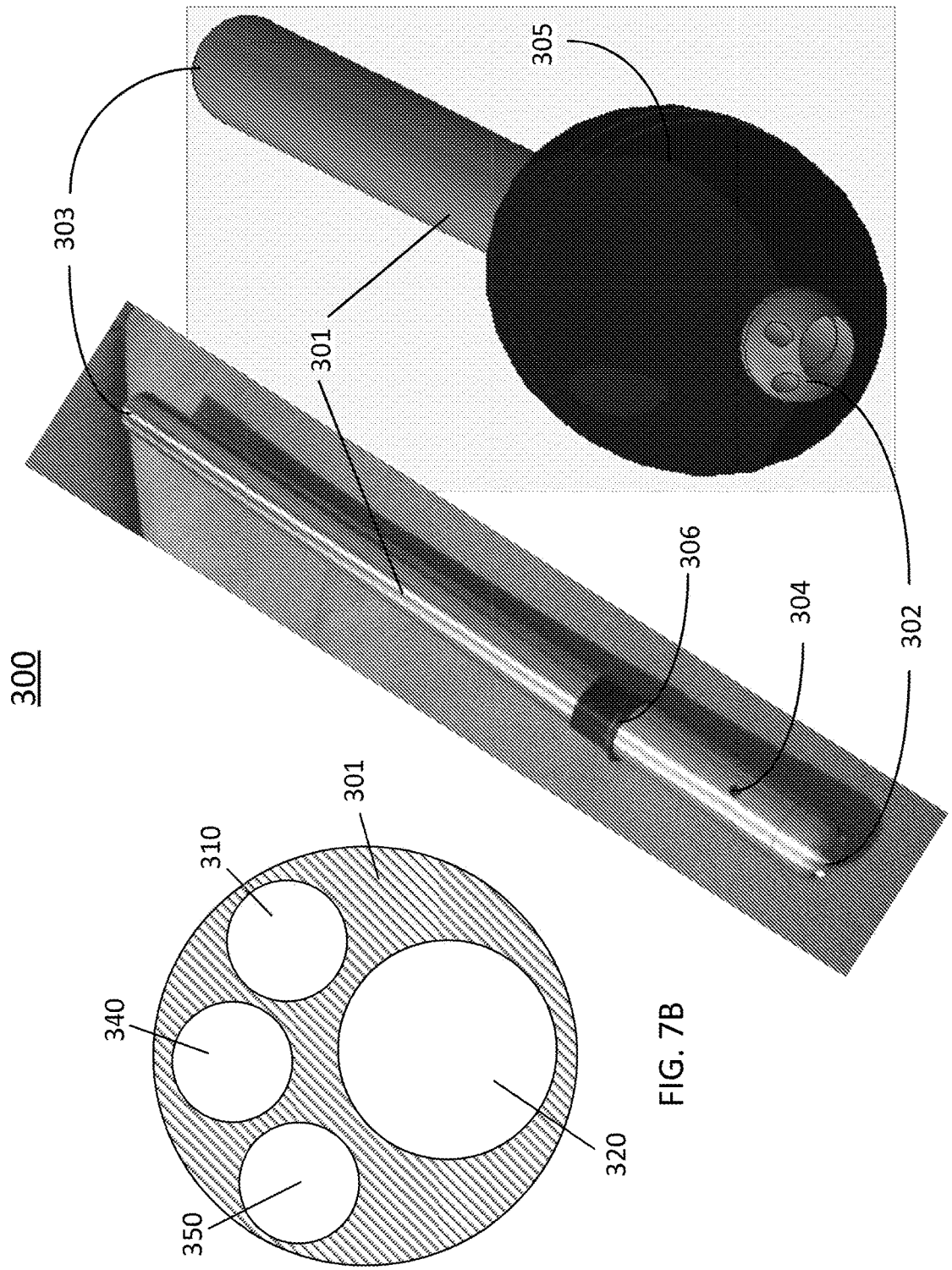

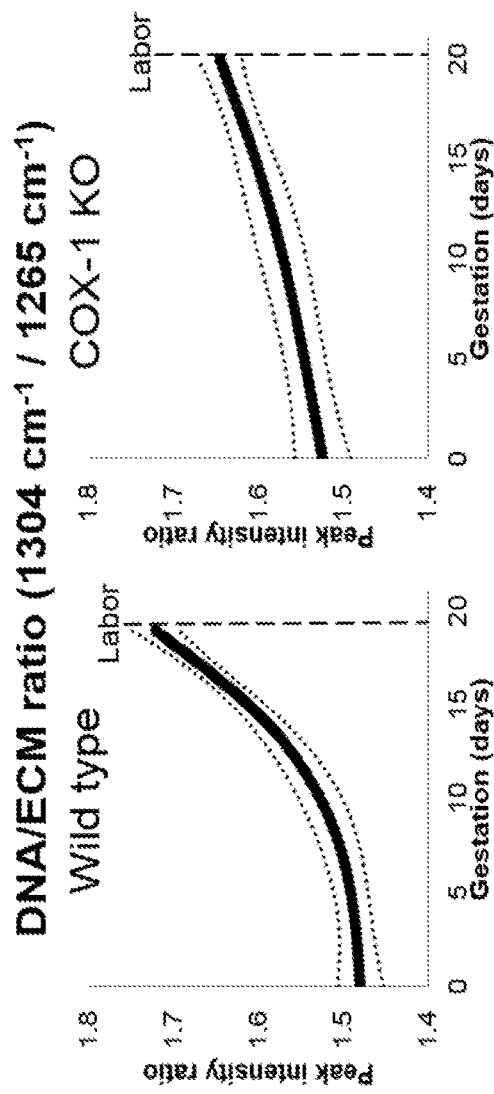 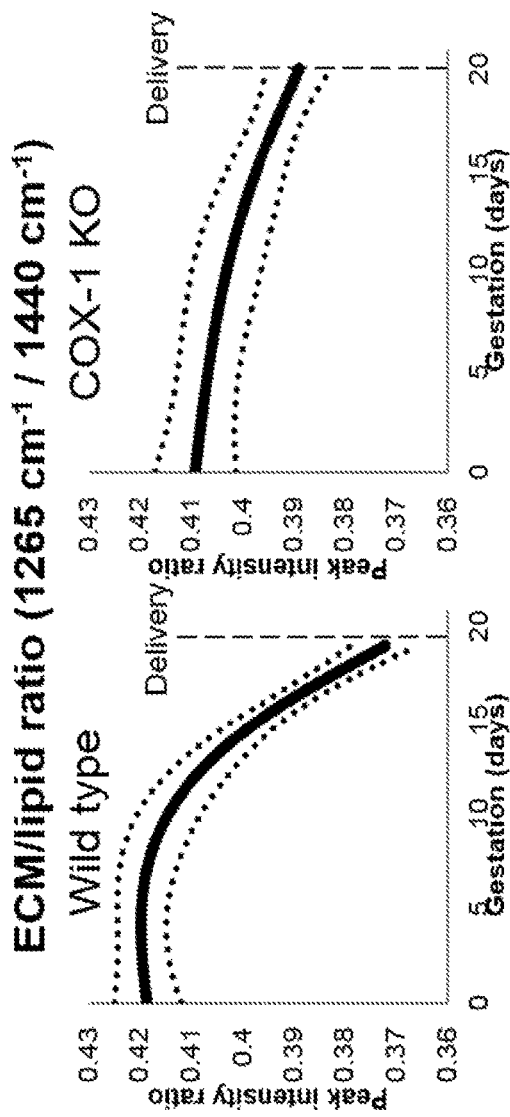
FIG. 11A
FIG. 11B

METHOD, SYSTEM AND SPECULUM-FREE OPTICAL PROBE FOR OPTICAL ASSESSMENT OF CERVIX, AND APPLICATIONS OF SAME

CROSS-REFERENCE TO RELATED PATENT APPLICATION

This PCT application claims priority to and the benefit of, U.S. Provisional Patent Application Ser. No. 62/508,049, filed May 18, 2017, entitled "SPECULUM-FREE DIAGNOSTIC PROBE FOR OPTICAL ASSESSMENT OF CERVIX AND APPLICATIONS OF SAME," by Christine O'Brien et al. The entire disclosure of the above-identified application is incorporated herein by reference.

Some references, which may include patents, patent applications, and various publications, are cited and discussed in the description of the present invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, [n] represents the nth reference cited in the reference list. For example, [50] represents the 50th reference cited in the reference list, namely, Mahadevan-Jansen A, Mitchell M F, Ramanujam N, Utzinger U, Richards-Kortum R. Development of a Fiber Optic Probe to Measure NIR Raman Spectra of Cervical Tissue In Vivo. Photochemistry and Photobiology. 1998; 68(3): 427-31. doi: 10.1111/j.1751-1097.1998.tb09703.x.

STATEMENT AS TO RIGHTS UNDER FEDERALLY-SPONSORED RESEARCH

This invention was made with government support under Contract No. (NSF Graduate Research Fellowship) awarded by the National Science Foundation. The government has certain rights in the invention.

FIELD OF THE INVENTION

The present invention relates generally to applications of Raman spectroscopy, and more particularly to speculum-free optical probes, methods and systems for using Raman spectroscopy to identify biochemical markers associated with cervical remodeling over the course of pregnancy of humans, and then assess whether a patient with pregnancy has risk of preterm birth, and applications of the same.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

Fifteen million babies were born prematurely in 2010, of which, 3.1 million died as a result of preterm birth (PTB) [1]. Even when the babies survive, PTB causes a myriad of short-term and long-term morbidities, including underdeveloped lungs, brain, and gastrointestinal tract, as well as an elevated risk for infection, resulting in medical costs over $26 billion annually in the United States alone [2]. The fetus needs at least 37 weeks to complete development and be ready to live without medical assistance outside of the womb; therefore, prolonging gestation to term (37 weeks) is important to ensure health of the fetus [3].

A variety of risk factors have been associated with PTB, including previous preterm birth, non-white race, poor nutrition, drug use, etc. [4, 5]. Cervical insufficiency is another risk factor in which the cervix cannot withstand the forces of pregnancy and ripens prematurely. Despite a plethora of risk factors, over half of spontaneous PTB (sPTB) cases (unexpected delivery) do not fall within any specific high-risk category, making the management of sPTB difficult [6]. The physician's goals in managing a patient with indications of labor before 37 weeks are to: (1) determine if the patient is actually experiencing preterm labor compared to normal discomforts of pregnancy that can be confused with labor symptoms, (2) identify the etiology of preterm labor (when feasible) as the management of each pathway is unique, and (3) provide pre-emptive pharmacologic (or surgical) therapy to prolong gestation such as tocolytics which suppress uterine contractions.

All tocolytic agents come with side effects, and no tocolytic can delay delivery indefinitely; however, increasing gestational age by even a few days can have a monumental impact on improving patient outcome. In addition to tocolytics, corticosteroids can be prescribed to improve respiratory outcomes in the infant [7]. Finally, antibiotics are commonly prescribed in case the patient has a subclinical infection, shown to be correlated with sPTB in many cases [7]. The efficacy of all the aforementioned pharmaceutical agents' these interventions increases when administered early, pointing to the need for recognizing early signs of PTB. Various clinical methods have been explored to estimate PTB risk, including monitoring uterine activity with a tocodynamometer, checking salivary estriol levels, measuring cervical length using transvaginal ultrasound, calculating cervical Bishop score via digital examination and screening for the presence of fetal fibronectin (fFN), a glue-like protein found in between the uterine lining and the fetal sac [8-11]. Of these, cervical length measurements have demonstrated the highest sensitivity (39%), and fFN screening has demonstrated the highest specificity (90%). However, these methods have a maximum accuracy of only 50% even when combined [8], underscoring the need for new technologies for improving our understanding of PTB and potentially predicting associated risk.

While labor and parturition is a coordinated process involving many systems and organs for proper function, it is only in recent years that researchers have begun to study the cervix for early signs of PTB. Regardless of etiology, all instances of sPTB with vaginal delivery require passage through the cervix. This fact is not trivial, as the cervix is a rigid structure with little compliance at the beginning of pregnancy, incapable of dilating even a few millimeters, let alone multiple centimeters. Ultrasound measurements of cervical length have demonstrated that cervical ripening occurs weeks prior to uterine contractions [12], supporting investigation of cervical remodeling during pregnancy as a pathway for predicting risk of PTB. Anatomically, the cervix is a cylindrical shaped organ including mainly extracellular matrix (ECM) that is infiltrated by cells, blood vessels, and a small amount of smooth muscle [13]. Biochemically, the most abundant component of the ECM is fibrillar collagen, accounting for 90% of the matrix proteins in the cervix [14]. Other important ECM components include elastin, hyaluronan, sulfated glycosaminoglycans, proteoglycans, and water. Current understanding of cervical changes during pregnancy is limited compared to our knowledge of other aspects of uterine biology, particularly in cases of cervical insufficiency and PTB. It is known that the normal process of cervical remodeling includes discrete stages (softening, ripening, dilation, and repair) that vary in duration between patients [15]. During the softening phase, hydration and vascularity increase, and the collagen matrix begins to remodel [15]. The ripening phase involves increased accumulation of hydrophilic molecules including glycosaminoclycans and hyaluronic acid, resulting in a further increase in cervical tissue hydration. Additionally, collagen becomes increasingly soluble. While the total amount of collagen remains the same, the collagen concentration decreases due to an influx of water and other matrix constituents [16]. Next, cervical dilation occurs as a rapid process in which the cervix can expand and dilate resulting in labor and delivery. Finally, cervical repair—the last phase—allows the rebounding of the collagen matrix which was degraded by an abundance of matrix metalloproteinases and leukocytes [17]. Collagen remodeling occurs in all phases of cervical maturation, and has been identified as the most important constituent governing mechanical strength in the cervix [18, 19]. A firm relationship has been established between the extent of collagen cross-linking and tensile strength in the pregnant mouse [20] and human cervix tissues [21-23]. However, it should be noted that these studies were performed on excised tissues and while they indirectly provide some information about tissue function and thus limit our ability to understand the processes that occur in vivo.

Many researchers are working to develop tools that can non-invasively evaluate cervical remodeling in vivo. These methods employ optical, ultrasonic and electrical phenomena to non-invasively interrogate the state of the cervix during pregnancy. An in-depth review of these methods can be found in Feltovich et al [24]. For example, electrical impedance has been measured in the cervix in pregnant women and was correlated to cervical hydration state [25]. While this is a promising method that provides a promising approach to study cervical hydration, it is limited in ability to monitor other biochemical and structural changes associated with cervical remodelling. Researchers have used various aspects of ultrasound, a well established clinical technique, to study cervical remodeling as well. For example, one group uses signal attenuation in transvaginal ultrasound images of the cervix to correlate with cervical hydration level [26] and backscattered power loss to provide information regarding the alignment of scatterers such as collagen fibrils, associated with cervical remodeling [27]. Ultrasound-based elastography has been used to estimate stiffness of the tissue [28]. Studies comparing induction patients revealed that those patients who had successful induction had a significantly higher elasticity index, indicating softer tissue, than patients with unsuccessful induction [28].

Direct mechanical testing of the pregnant cervix has been used to estimate cervical stiffness by measuring the pressure required to displace cervical tissue by a pre-set amount and results from this work have demonstrated the ability to detect decreasing levels of stiffness over the course of pregnancy [29]. Other groups have developed cervical dilators that measure cervical resistance index, which is the force required to dilate the cervix by a total of 8 mm [30]. Significant differences in cervical resistance index, between non-pregnant patients without abnormal obstetric history and non-pregnant patients with history of spontaneous mid-trimester abortions have been reported. Mathematical models have been developed to predict patient outcome and assess risk of preterm birth [22, 31]. All of these methods including ultrasound offer important biomechanical information, but cannot be used to monitor the biochemical and molecular dynamics in the cervical remodelling process.

Optical methods use light to probe tissue morphology and biochemistry depending on the light-tissue interaction process used. Three primary optical methods have been explored to study PTB. The collascope, a device that excites collagen and measures light-induced fluorescence, can monitor the state of collagen in the cervix during pregnancy [32]. Collagen is a natively fluorescent protein, with insoluble collagen having higher fluorescent intensity than soluble collagen. As collagen solubility increases with cervical ripening, the intensity of fluorescence decreases both in mice and in humans [32-34]. In addition to being an intrinsically fluorescent protein, collagen type 1 is capable of second harmonic generation (SHG) and can produce a strong signal with very little background if excited at the appropriate wavelengths. SHG has been used to study the cervix of pregnant mice in vivo and has been demonstrated in ex vivo human cervical samples. It is capable of producing high resolution images of cervical collagen and the results have verified that the collagen networks in the cervix become increasingly disorganised with advancing gestation [35, 36]. Near-infrared spectroscopy has been used to monitor haemoglobin, water and optical scatterers in the pregnant cervix, by measuring the diffuse reflectance of light at various near-infrared wavelengths [37, 38]. Preliminary studies found increasing values for light scattering and haemoglobin over the course of pregnancy and observed an increase in cervical hydration during cervical ripening with misoprostol [37, 38].

Incomplete understanding of cervical remodeling and the parturition process hinders our ability to evaluate PTB risk in patients and therefore reduce the unacceptably high prevelance, morbidity, and mortalty caused by preterm birth. This prevents us from developing effective diagnostics and therapeutic interventions because we do not know what their targets should be. Unfortunately, classically used basic science methods have not yet been able to solve this problem, partially due to their invasive nature. Few existing approaches have offered the ability to monitor cervical changes over time within the same subject, while fewer have been capable of probing the biochemical environment.

Thus, there is a need for the application of new methods to improve our understanding of the cervical remodeling process and potentially enable in vivo human cervix monitoring.

SUMMARY OF THE INVENTION

In one aspect, the invention relates to a method for identification of biochemical markers associated with cervical remodeling over the course of pregnancy of humans. In one embodiment, the method includes obtaining Raman signals from the cervix of each of a group of humans with pregnancy at each phase of pregnancy; finding Raman signatures corresponding to each type of cervical tissue from the obtained Raman signals; and identifying biochemical markers associated with cervical remodeling at each phase of pregnancy corresponding to the Raman signatures.

In one embodiment, each of Raman signals is obtained by delivering a beam of light at a predetermined wavelength to the cervix to illuminate the cervix therewith; collecting light scattered from the cervix responsive to the illumination of the beam of light; and obtaining the Raman signal from the scattered light.

In one embodiment, the delivering and collecting is performed by a speculum-free optical probe.

In one embodiment, the predetermined wavelength comprises a wavelength in a near-infrared range.

In one embodiment, the Raman signals comprises Raman spectra, and wherein the finding step comprises processing the obtained Raman spectra to find the Raman signatures corresponding to each type of the cervical tissue. In one embodiment, the Raman signatures comprise peaks and their corresponding wavelengths in the Raman spectra, wherein each peak and the corresponding wavelength correspond to a Raman band of a corresponding type of cervical tissue.

In one embodiment, the method further includes characterizing changes and trends of the biochemical markers over the course of pregnancy.

In one embodiment, the method further includes correlating the biochemical markers with clinical measures of pregnancy and outcomes.

In one embodiment, the biochemical markers are associated with collagen, lipids, nucleic acids and other proteins relevant to each phase of the cervical remodeling.

In one embodiment, the method further includes comprising analyzing a longitudinal progression of cervical change using a generalized linear model (GLM) that satisfy $$Y=\beta X+\varepsilon$$

wherein Y is a vector containing the Raman signals, X is a matrix containing independent variables including gestational age, body mass index (BMI), and parity, $\beta$ is a vector containing weight coefficients of the independent variables, and $\varepsilon$ is a residual error in the GLM, wherein a linear least square regression is performed to choose the weight coefficients of $\beta$ such that $\varepsilon$ is minimized. In one embodiment, the method further includes correlating the Raman signals with measures of cervical length and Bishop score.

In one embodiment, the group of humans is with normal pregnancy, or with high risk pregnancy of preterm birth (PTB). In one embodiment, the method further includes correlating spectral changes from the group of humans with normal pregnancy and the group of humans with high risk pregnancy of PTB with clinical measures and biochemical markers so as to characterize their trends of changes in the group of humans with high risk pregnancy of PTB.

In another aspect, the invention relates to a method for assessing whether a patient with pregnancy has risk of PTB. In one embodiment, the method includes obtaining Raman signals from the cervix of the patient at each phase of pregnancy; finding Raman signatures corresponding to each type of cervical tissue from the obtained Raman signals; identifying biochemical markers associated with cervical remodeling at each phase of pregnancy from the Raman signatures; and determining deviations of the biochemical markers so as to assess whether the patient has the risk of PTB.

In one embodiment, each of Raman signals is obtained by delivering a beam of light at a predetermined wavelength to the cervix to illuminate the cervix therewith; collecting light scattered from the cervix responsive to the illumination of the beam of light; and obtaining the Raman signal from the scattered light.

In one embodiment, the delivering and collecting is performed by a speculum-free optical probe.

In one embodiment, the predetermined wavelength comprises a wavelength in a near-infrared range.

In one embodiment, the Raman signals comprises Raman spectra, and wherein the finding step comprises processing the obtained Raman spectra to find the Raman signatures corresponding to each type of the cervical tissue.

In one embodiment, the Raman signatures comprise peaks and its corresponding wavelengths in the Raman spectra, wherein each peak and the corresponding wavelength correspond to a Raman band of a corresponding type of cervical tissue.

In one embodiment, the biochemical markers are associated with collagen, lipids, nucleic acids and other proteins relevant to each phase of the cervical remodeling.

In one embodiment, the determining step comprises comparing the biochemical markers with a library of biochemical information that contains the biochemical markers associated with cervical remodeling over the course of pregnancy of humans to determine the deviations of the biochemical markers.

In yet another aspect, the invention relates to system for assessing whether a patient with pregnancy has risk of PTB. In one embodiment, the system has an optical probe optically connected to a light source and configured to deliver a beam of light emitted from the light source to the cervix of the patient to illuminate the cervix therewith and to collect light scattered from the illuminated cervix; a detector optically coupled with the optical probe, for obtaining Raman singals from the collected scattered light; and a controller in communication with the detector and programmed to find Raman signatures corresponding to each type of cervical tissue from the obtained Raman signals; identify biochemical markers associated with cervical remodeling at each phase of pregnancy corresponding to the Raman signatures; and determine deviations of the biochemical markers so as to assess whether the patient has the risk of PTB.

In one embodiment, the light source comprises a laser or light emitting diodes (LEDs).

In one embodiment, the beam of light has a wavelength in a near-infrared range.

In one embodiment, the optical probe is speculum-free optical probe and has a working end, a housing, a delivery and collection means, a camera, and at least one rinse channel received in the housing, wherein the working end is operably positioned proximate to a surface of the cervix of the patient.

In one embodiment, the delivery and collection means comprises a plurality of fibers, wherein at least one fiber of the plurality of fibers is configured to deliver the beam of light emitted by the light source from the working end to the surface of the cervix so as to illuminated the cervix therewith, and the remaining fibers of the plurality of fibers are configured to collect from the working end light scattered from the illuminated cervix.

In one embodiment, the plurality of optical fibers is spatially arranged in a fiber array. In one embodiment, the at least one fiber for delivering the beam of light is positioned in a center of the fiber array, and the remaining fibers or collecting the scattered light are positioned in one or more rings surrounding the at least one fiber.

In one embodiment, the at least one rinse channel is adapted to apply saline or the like to clean tissue of the cervix.

In one embodiment, the working end of the optical probe is flat or rounded.

In one embodiment, the camera comprises a fiber camera, or an endoscopic camera.

In one embodiment, the optical probe further comprises a series of white light LEDs received in the housing and surrounding the camera.

In one embodiment, the optical probe further comprises an inflatable balloon placed at the working end for blocking environmental light.

In one embodiment, the detector comprises a spectrometer.

In one embodiment, the detector further comprises a CCD.

In one aspect, the invention relates to a speculum-free optical probe. In one embodiment, the speculum-free optical probe has a working end, a housing, a delivery and collection means, a camera, and at least one rinse channel received in the housing, wherein the working end is operably positioned proximate to target tissue.

In one embodiment, the delivery and collection means comprises a plurality of fibers, wherein at least one fiber of the plurality of fibers is configured to deliver the beam of light emitted by the light source from the working end to the target tissue so as to illuminated the target tissue therewith, and the remaining fibers of the plurality of fibers are configured to collect from the working end light scattered from the illuminated target tissue.

In one embodiment, the plurality of optical fibers is spatially arranged in a fiber array. In one embodiment, the at least one fiber for delivering the beam of light is positioned in a center of the fiber array, and the remaining fibers or collecting the scattered light are positioned in one or more rings surrounding the at least one fiber.

In one embodiment, the at least one rinse channel is adapted to apply saline or the like to clean the target tissue.

In one embodiment, the working end of the optical probe is flat or rounded.

In one embodiment, the camera comprises a fiber camera, or an endoscopic camera.

In one embodiment, the speculum-free optical probe further has a series of white light LEDs received in the housing and surrounding the camera.

In one embodiment, the speculum-free optical probe further has an inflatable balloon placed at the working end for blocking environmental light.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

FIGS. 7B-7D show a cross-sectional view (FIG. 7B) and two perspective views (FIGS. 7C-7D) of a speculum-free optical probe according to another embodiment of the invention

FIGS. 11A-11B respectively show modeled longitudinal trajectories of cervical change in COX-1 KO mice (FIG. 11A) and wild type mice (FIG. 11B) throughout pregnancy.

DETAILED DESCRIPTION OF THE INVENTION

Figure 1A:
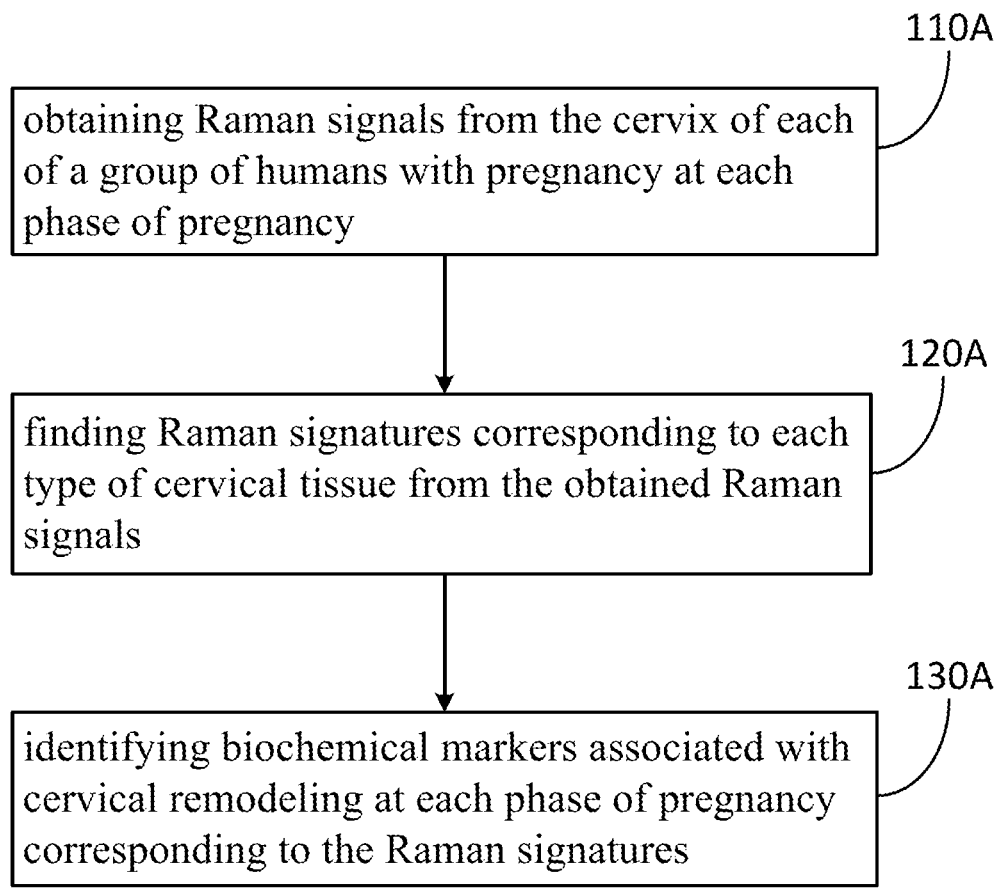
FIG. 1A shows a flowchart for identifying biochemical markers associated with cervical remodeling over the course of pregnancy of humans according to one embodiment of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification. It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which the present invention belongs. It is further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Figure 2:
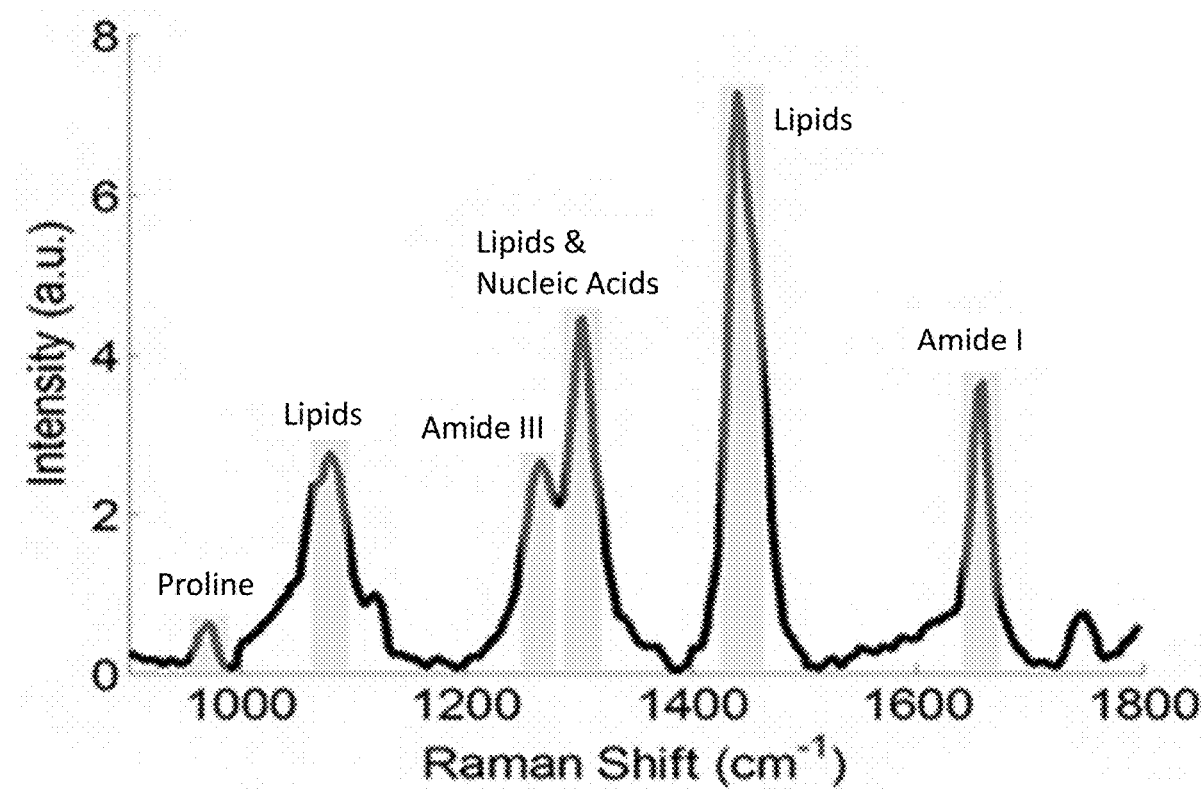
FIG. 2 shows a Raman spectrum collected from in vivo mouse cervical tissue.
Figure 3A:
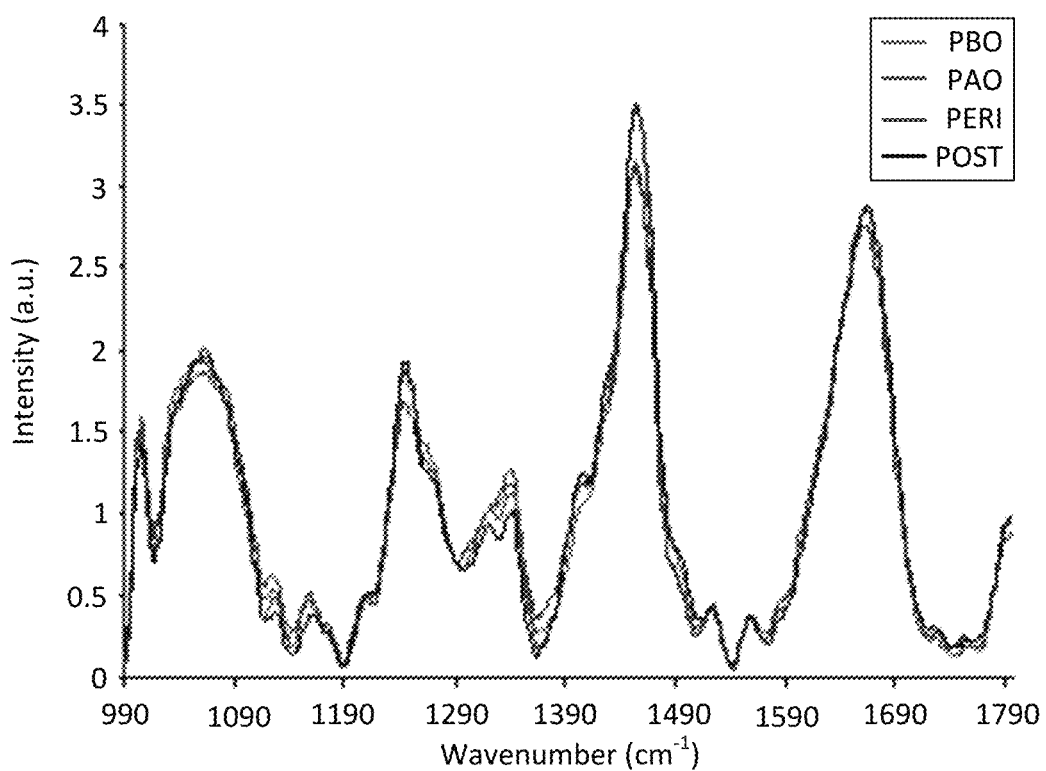
FIG. 3A shows Raman spectra acquired from the normal non-gravid human cervix.
Figure 3B:
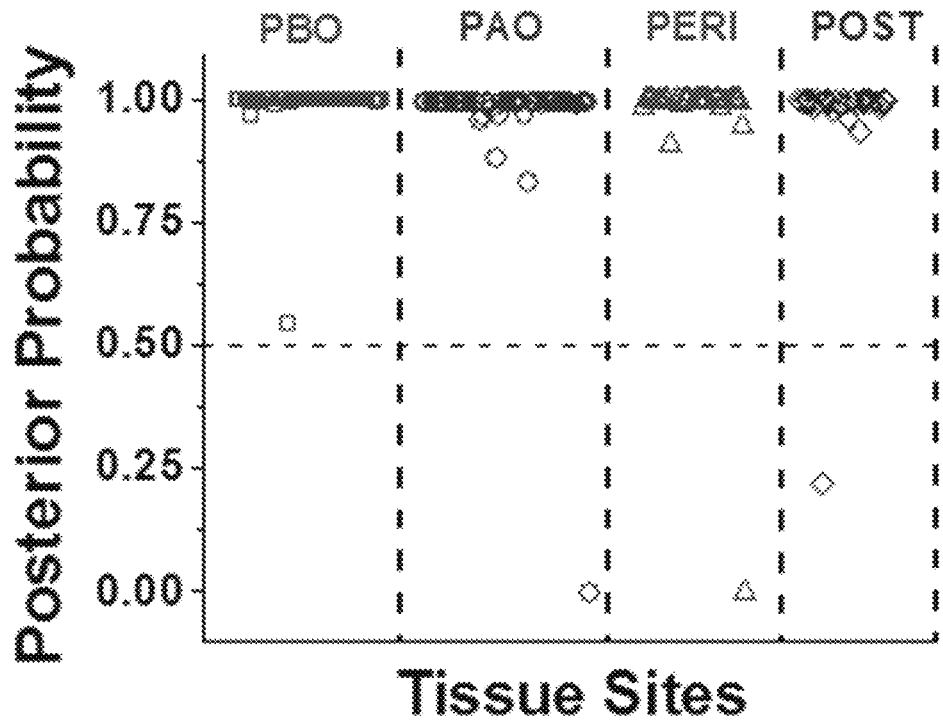
FIG. 3B shows the Raman spectra statistically assigned to specific hormonal categories using a Bayesian approach with a classification accuracy of over 98%, PBO: pre-menopause before ovulation; PAO: pre-menopause after ovulation; PERI: peri-menopause; POST: post-menopause [48].

Raman spectroscopy (RS) is an inelastic scattering technique that probes the vibrational energy levels of molecules. A Raman spectrum includes spectrally narrow peaks which correspond to the different vibrational modes of molecules and yield sample-specific molecular fingerprints, from which biochemical composition and related structure can be ascertained. As shown in FIG. 2, RS generates signals corresponding to lipids, proteins, and nucleic acids, offering direct information regarding the biochemical state of the tissue. For example, when malignant cells begin to "crowd", their nucleus-to-cytoplasmic ratio increases, which is detected by a change in Raman peaks characteristic of nucleic acids [39]. Due to its high sensitivity and specificity, RS has been increasingly used in biomedical applications. RS has been used to detect disease in various organs such as the cervix, bladder [40, 41], oesophagus [42, 43], skin [44, 45], breast [46] and gastrointestinal tract [47]. Development of a fiber optic probe has enabled its use in vivo, with applications in many organ systems in animal models as well as humans. Dr. Mahadevan-Jansen was one of the first to successfully demonstrate the application of RS to detect cervical dysplasia in vivo in human patients. She was also the first to demonstrate that RS is sensitive enough to detect the effects of hormonal status on healthy tissue [48] as use this information to improve disease detection. However, it is only recent years that there has been interest in using this technique to understand physiological processes. In a recent study, RS is used to measure the composition and mechanical properties of young and aging bone [49]. When studying bone, measures such as mineral-to-matrix ratio and collagen quality are used to correlate tissue biochemistry to biomechanical properties. These calculated values are being investigated as sensitive predictors of bone fracture risk for osteoporosis patients. RS applied to the in vivo cervix for the diagnosis of cervical dysplasia by Dr. Mahadevan-Jansen [50, 51] displays remarkable accuracy for detecting cervical abnormalities and was able to classify normal, and high-grade dysplasia with high accuracy [52]. However, low grade dysplasia demonstrated a poorer sensitivity. In an attempt to improve classification accuracy particular of low grade dysplasia, the effect of hormonal status on Raman spectra was evaluated [48]. Spectra from non-gravid patients with normal Pap testing results were classified based on hormonal status with 98% accuracy (FIGS. 3A-3B) [48]. Accounting for hormonal status in dysplasia patients resulted in an increase in classification accuracy from 88% to 94% [53]. To further improve classification accuracy, four more patient variables were studied: body mass index (BMI), obstetric history, ethnicity, and socioeconomic status, of which only obstetric history and BMI were found to have an impact on Raman spectra [54]. These findings, in addition to the influence of hormonal status, indicate RS can be used to study the pregnant cervix.

Figure 4A:
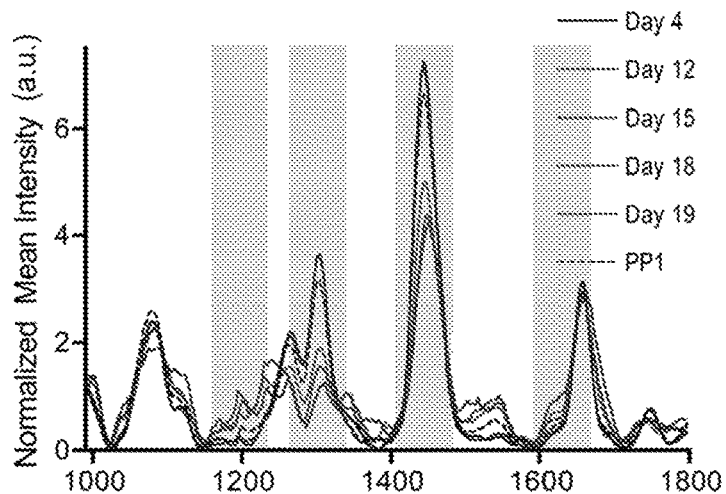
FIGS. 4A-4C respectively show (FIG. 4A) Raman spectra of the in vivo mouse cervix. Gray regions indicate significant difference over gestation ($p<0.1$), (FIG. 4B) Plot of spectral peak values from the 1308 $cm^{-1}$ associated with lipids, and (FIG. 4C) Cervical stiffness, measured from stress-strain curves in tensile testing. Raman spectroscopy and tensile strength are in strong agreement [55].
Figure 4B:
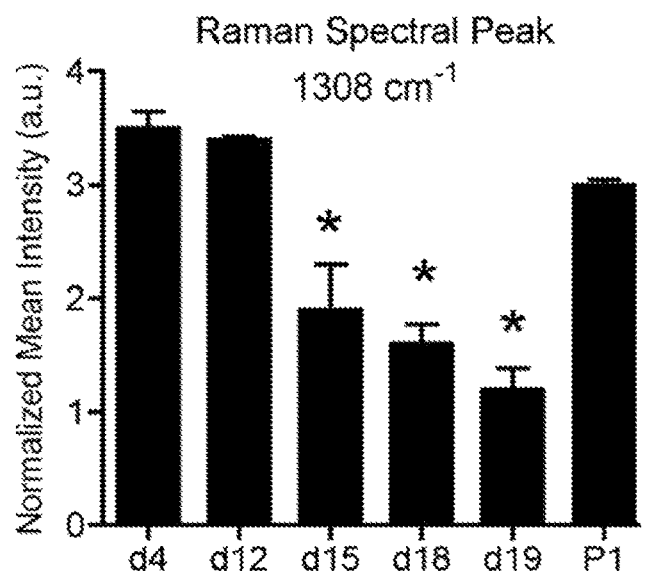
Figure 4C:
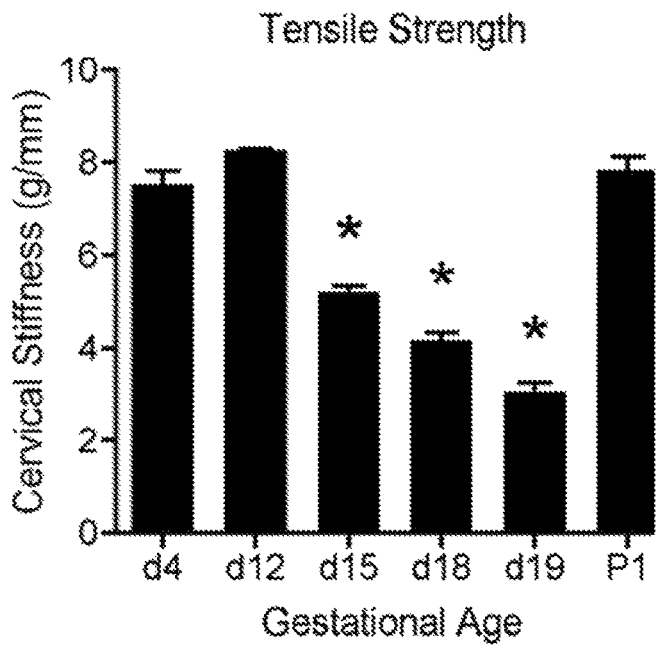

A pilot study was conducted in which Raman measurements were taken from the in vivo cervix of wild type mice throughout gestation (FIG. 4A) [55]. Statistically significant differences were observed over the course of gestation from many Raman peaks, including peaks specific to lipids, nucleic acids, and collagen. The 1308 cm$^{-1}$ lipid peak displayed a decreasing intensity (FIG. 4B) with a trend similar to that observed when compared to tensile testing which was performed at the same time points and used as the gold standard for quantifying cervical change (FIG. 4C). These results in mice provided evidence that RS is indeed capable of detecting changes in the cervix during pregnancy and motivated the need for further study particularly in humans.

The objectives of the invention is to use RS to study pregnancy in humans so as to understand cervical remodeling during parturition in humans in vivo by characterizing the biochemical markers associated with each phase of pregnancy, e.g., the biochemical markers that occur during the four stages of cervical remodeling in healthy pregnancies, and identify Raman spectral markers indicative of early signs of PTB to predict risk, which determines how these changes deviate in high risk populations.

In certain aspects, the invention provides a fiber optical probe and a portable fiber optical probe-based Raman Spectroscopy system for acquiring Raman spectra from patients for achieving the objectives.

Figure 7A:
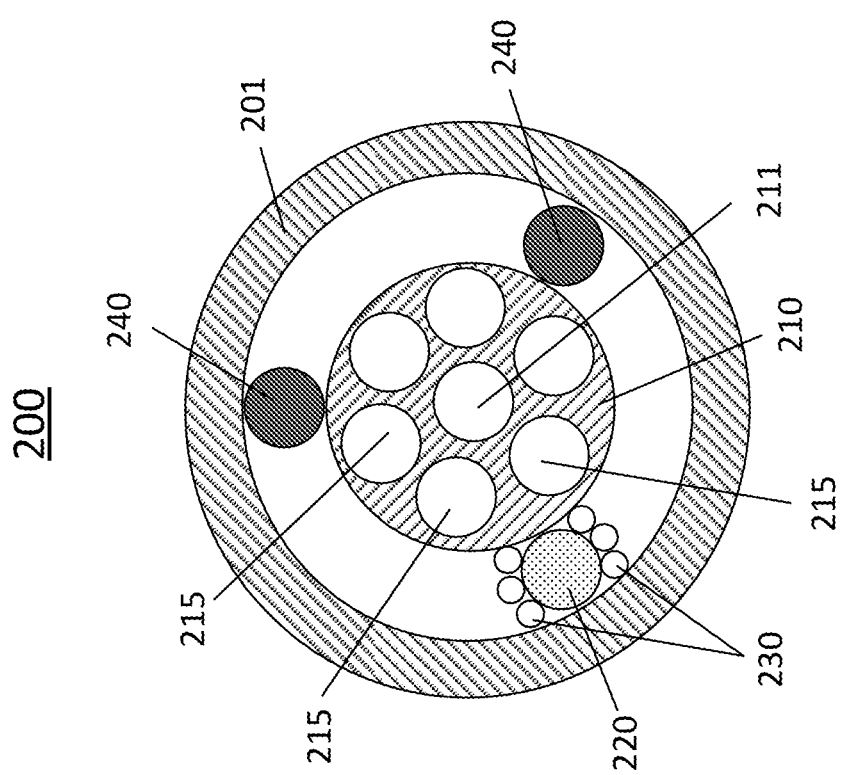
FIG. 7A shows a cross-sectional view of a speculum-free optical probe according to one embodiment of the invention.

In one embodiment, the fiber optical probe is a speculum-free integrated optical probe. As shown in FIG. 7A, the speculum-free optical probe 200 includes a fiber probe (i.e., delivery and collection means) 210 having a plurality of optical fibers 211 which at least one fiber 211 is for excitation and the other fibers 215 are data collection, a camera 220, a series of white light LEDs 230, and one or more rinse channels 250. The camera 220 is a fiber based camera used to visually guide the placement of the fiber probe 210 under white light illumination emitted from the series of white light LEDs 230. The camera 220 may also be used to acquire images of the cervix. The camera 220 can also be other types of cameras. The rinse channels 250 are used to apply saline or the like to clear the cervix of any debris and mucous prior to placing the fiber probe 210 in contact with the tissue.

In the exemplary embodiment shown in FIG. 7A, the speculum-free optical probe 200 further has a proximal end, a working end (a distal end) at which the camera 220 is placed and the excitation and data collection are performed, and an opposite, (not shown) and a probe housing 201 having a plurality of lumens/channels extending between the proximal end and the working end for housing the fiber probe 210, the camera 220, the series of white light LEDs 230 and the rinse channels 250, respectively. In certain embodiments, the working end of the speculum-free optical probe 200 is flat or rounded. In one embodiment, the speculum-free integrated optical probe 200 is about 5 mm in diameter and disinfectable as required for routine care. The speculum-free optical probe 200 may have other sizes of diameters. In certain embodiments, the speculum-free optical probe 200 can be flexible or rigid. In addition, speculum-free optical probe 200 is also biocompatible.

In operation, the speculum-free integrated optical probe 200 is guided along the fingers of the provider under visual guidance with the built-in camera. Once the working end of speculum-free optical probe 200 is in gentle contact with the ectocervix, the overhead lights are turned off and multiple Raman spectra are acquired.

In certain embodiments, the speculum-free optical probe 200 also allows for optical data collection such as fluorescence spectroscopy, microendoscopy, diffuse reflectance spectroscopy, etc., from the human cervix in vivo without the use of a speculum exam.

FIGS. 7B-7D show another embodiment of a speculum-free optical probe 300 according to the invention, which has an access tube (or a probe housing) 301 having a proximal end 303, a working end (a distal end) 302, and a plurality of lumens/channels extending between the proximal end 303 and the working end 302. The access tube 301 is formed of a material that is biocompatible. In the exemplary embodiment shown in FIGS. 7B-7D, four channels are included. The first channel 320 is an imaging channel and houses an endoscopic camera that allows for visualization during the procedure, and eliminates the need for colposcope. Once the speculum-free optical probe 300 is inserted and the cervix has been identified, the practitioner inflates a balloon 305 placed at the working end 302 of the access tube 301 using a hand pump that connects through a valve at the proximal end 303 of the access tube 301. The valve is connected to the inflatable by the second channel 350 that runs inside the access tube 301 to an opening 304 on the outside of the access tube 301 near the working end 302 of the access tube 301. Air runs form the hand pump, down the second channel 350, out of the hole in the side of the access tube 301 and inflates the balloon 305, as shown in FIG. 7D. The inflatable includes a latex (or latex-free substitute) sleeve 306 that runs along about 4 cm (or other centimeters) of the access tube 301 starting from the working end 302. Upon inflation the balloon 305 opens up the vaginal canal nearest the cervix and allows for visualization of the entire cervix. A third channel 340 contained within the access tube 301 then allows the practitioner to clean the cervix with a pressurized fluid stream. Operably, Saline solution is flushed through third channel 340 for cleaning target tissue. In addition, an acetic acid stain is also applied to the cervix through the third channel 340 for visualizing abnormalities. The camera in the first channel 320 allows the practitioner to easily identify abnormalities on the cervix. Once a tissue target is identified, the Raman probe placed in the fourth channel 310 is directed toward the tissue target guided by the visual feedback from the camera in the first channel 320. In one embodiment, the Raman probe includes a plurality of optical fibers which one fiber includes a 785 nm laser or is for delivery of light of a wavelength of 785 nm emitted from a laser and the other fibers are for data collection. Because of the novel inflatable design, the practitioner no longer relies on the removal of ambient light from the exam room for accurate Raman measurements, as complete darkness is obtained at the sampling site due to the light-blocking properties of the inflatable. Upon completion of the measurements, the balloon 305 can be quickly deflated for easy removal of the access tube 301.

Conventionally, the procedure for carrying out Raman spectroscopy of cervical tissue requires a speculum exam to visualize and clean the cervix prior to collecting data. However, a speculum exam is painful, invasive, time-consuming to perform, and not proven to be safe on patients that are at less than 37 weeks' of pregnancy. However, the invented optical probe is a speculum-free optical probe that increases clinical translatability and safety and allows midwives, nurse practitioners, and nurses to use it in addition to physicians, and also greatly increases patient comfort.

According to embodiments of the invention, the speculum-free optical probe combines various components of the procedure, such as visualization of the cervix, cleaning of the cervix, displacement of vaginal tissue for line-of-sight access to the cervix, and Raman measurement, into one easy-to-use device. The speculum-free optical probe allows optical images to be taken from parts of the body that are not easily visualized, because it incorporates a camera and white light visualization guidance component. In addition, speculum-free optical probe also allows researchers and providers to ensure that the cervix is clean prior to data collection, which overcomes the problem of contamination of data collection by biological specimens.

In certain aspect, the innovation of the invention is directly targeted for implementation of optical diagnostics in women's health care so that in vivo measurements of tissues may be made with minimal interference to clinical workflow and little or no discomfort to the patient. This optical probe obviates speculum exams for optical cervical assessment by incorporating a visual guidance and cleaning system that can be gently inserted during a digital exam. The optical probe allows for optical data collection, such as Raman spectroscopy, fluorescence spectroscopy, microendoscopy, diffuse reflectance spectroscopy, etc., from the human cervix in vivo without the use of a speculum exam. The optical probe has several features, including visual guidance, saline rinse capabilities so that the practitioner can clean the cervix of blood and mucus, and fiber optics or optical detectors for performing optical assessment of cervical tissue. This technology is incorporated into the provider's regular bimanual exams that are routinely performed during women's health exams, and it allows visual and optical assessment of cervical tissue without the need for an invasive, uncomfortable speculum exam. Once the cervix is identified using visual guidance, the practitioner can use a built-in saline rinse to clean the cervix and will then perform optical measurements.

Among other things, the optical probe has at least the following features. The optical probe eliminates a speculum exam from optical data collection from the cervix. The synthesis of various aspects of the current optical assessment protocols allows each element (visual guidance, cleaning, optical measurement) to be accurately placed and inserted together. A reduction in the number of instruments inserted into the vaginal canal will lower risk of infection and adverse events (accidentally rupturing membranes during pregnancy) during cervical assessment. The first report of speculum-free optical assessment of the in vivo cervix is reported using this device. This device has been carefully designed to promote patient comfort and clinician ease of use. The inflatable design, in conjunction with the method of inflating it through the inner channel, provides the required vaginal canal clearance for inspection of the cervix, while minimizing the demands on the patient. This inflatable has a width of between 2-3 inches and therefore, eliminates the need to apply great pressure to the vaginal opening, the most sensitive region of the canal. Further, this design accomplishes the light-blocking required to facilitate the adoption of Raman spectroscopy for cervical analyses. The access tube synthesizes various aspects of the existing Raman protocol, while introducing the potential for new and improved processes, such as the removal of cervical mucus using a syringe, within a single access tube. This allows for the tools to be more accurately placed and inserted together, rather than individually as currently is the standard. The potential to use a camera provides the benefits of endoscopy, particularly closer examination of abnormalities.

Accordingly, the invented optical probe has advantages over the conventional approaches.

Previously the procedure for carrying out Raman spectroscopy of cervical tissue was a complicated and inefficient procedure. This optical probe combines the various components of the procedure (visualization of the cervix, cleaning of the cervix, displacement of vaginal tissue for line-of-sight access to the cervix, light blockage, and Raman measurement) into one easy to use device.

For procedures necessitating cervical access, a speculum is typically used to displace vaginal tissue, which causes significant patient discomfort. The inflatable design involved in this technology carries out this function while avoiding pressure on sensitive areas of the female anatomy like the vaginal opening.

Accurate Raman spectroscopy requires complete darkness. The existing protocol requires the practitioner carrying out the test to turn off room lights, and assume no other light source is present. This technology ensures complete darkness at the test site on the cervix without having to turn off room lights or concern for other ambient light sources.

The optical probe allows visualization of the cervix using an endoscopic camera.

The optical probe enables the cervix to be cleansed of mucous by a pressurized fluid stream instead of the conventional cotton swab method.

The optical probe, however, are the synthesis of the commonly accepted practice of endoscopy, with the failed attempts at developing an inflatable speculum, along with access for both a spray syringe to clean the cervix pre-measurement and the currently-used fiber optic Raman probe. The design of the access tube allows these devices to be introduced to the cervix simultaneously, while also minimizing the size of the intruding device.

The optical probe enables easy delivery of the Raman probe to a cervical tissue site. With regards to the inflatable, there are a number of inflatable speculum inventions. However, these continue to function along the full length of the canal, as a traditional speculum, and do not provide the improvement on patient comfort seen from our smaller expansion at the mouth of the cervix. None of these have been shown to effectively block light from the cervix either. Compared to a traditional speculum, the inflatable provides greatly reduced patient discomfort, as the walls are not forced to be expanded as greatly. This also cuts down on the avenues for light to travel to the cervix, a key for this inventions potential application with Raman spectroscopy.

In certain aspects, the invention also relates to a system including the speculum-free optical probe for facilitation of Raman spectroscopy to evaluate biochemical markers associated with cervical remodeling during normal human pregnancy, and identify PTB biomarkers in the human cervix from high risk pregnancies.

Figure 8:
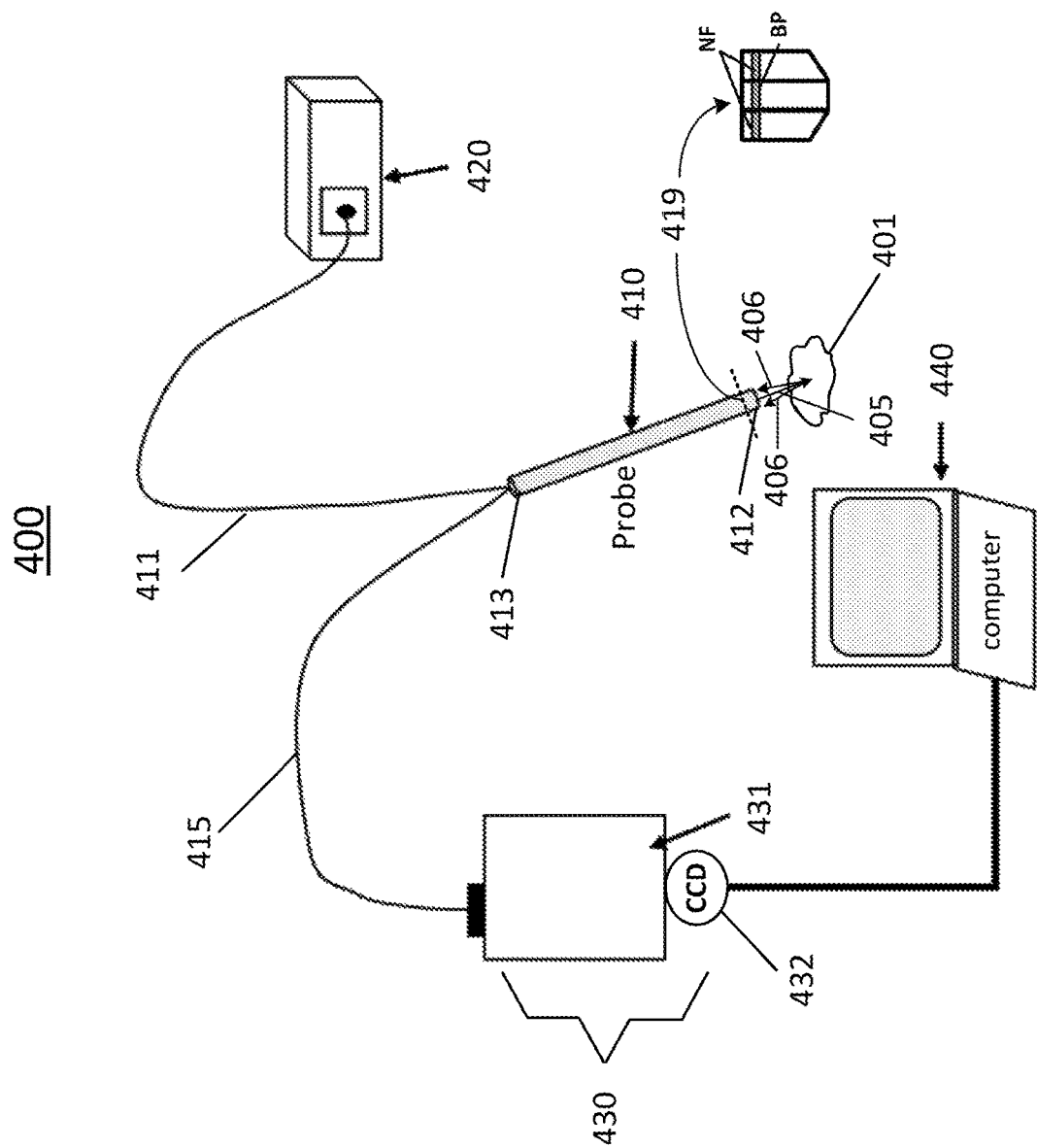
FIG. 8 shows schematically a portable Raman system used for human data collection according to one embodiment of the invention.

In one embedment as schematically shown in FIG. 8, the system 400 includes a fiber optic probe 410, a light source 420, a detector 430 and a computer 440. In the exemplary embodiment, the detector 430 includes a charge coupled device (CCD) camera 432, and an imaging spectrograph 431 coupled to the air-cooled back-illuminated, deep-depletion charge coupled device (CCD) camera 432, which is controlled with the computer 440 for processing Raman signals. Other types of detectors can also be used to practice the invention.

The light source 420 is adapted to provide a beam of light with appropriate excitation wavelengths and energy so as to excite certain molecules of tissue 401, when receiving the beam of light, to generate Raman reflections. In this embodiment, the light source 420 is a diode laser capable of generating a beam of laser light with wavelength 785 nm. Other suitable light sources can also be utilized to practice the present invention.

The fiber optic probe 410 has a plurality of optical fibers. Of them, one optical fiber 411 optically couples the light source 420 for delivering a beam of light 405 emitted from the light source 420 to the target of tissue 401 through the working end 412. The other optical fibers are adapted for collecting optical signals 406 emitted from the tissue 401 responsive to the incident beam of light 405. The collected optical signals 406 are then sent to the spectrograph 431 through one or more fibers 415 for recording, processing and displaying the optical signals. In one embodiment, the working end 412 of the fiber optic probe 410 is configured with inline filtering means 419 including a noise filter (NF) and/or a band pass (BP) to maintain the quality of the optical signals, and minimize interference from the components used in the fiber optic probe 410 itself.

In certain embodiments, the CCD 432 and the computer 440, adapted with appropriate controller cards and software to control signal acquisition, process data and display spectra, are utilized to process and display images corresponding to the optical signals 406 emitted from the tissue 401, which may guide a surgeon or a medical professional through a medical procedure to identify tissues and act on them accordingly.

Spectra are calibrated using standard protocols and processed for fluorescence subtraction and noise smoothing [56].

In certain aspects of the invention, RS is used to study pregnancy and preterm birth in humans. Among other things, cervical remodelling is studied and the biochemical markers that change with pregnancy are characterized using RS. In certain embodiments, the functionality of RS is expanded as applied to humans in vivo, through several distinct features of technical and applied innovation regarding the investigation of cervical remodeling. The results have direct implications in the assessment of risk for preterm birth and may impact the development and refinement of new or current methods of treatment. Biochemical markers are identified that can potentially facilitate the application of RS as a non-invasive method that can predict risk.

Referring to FIG. 1A, a method for identification of biochemical markers associated with cervical remodeling over the course of pregnancy of humans is shown according to one embodiment of the invention. In the exemplary embodiment, the method includes the following steps.

At step 110A, Raman signals are obtained from the cervix of each of a group of humans with pregnancy at each phase of pregnancy.

In some embodiments, each of Raman signals is obtained by delivering a beam of light at a predetermined wavelength to the cervix to illuminate the cervix therewith; collecting light scattered from the cervix responsive to the illumination of the beam of light; and obtaining the Raman signal from the scattered light.

In some embodiments, the delivering and collecting is performed by a speculum-free optical probe.

In some embodiments, the predetermined wavelength comprises a wavelength in a near-infrared range.

At step 120A, Raman signatures corresponding to each type of cervical tissue are found from the obtained Raman signals.

In some embodiments, the Raman signals comprises Raman spectra, and wherein the finding step comprises processing the obtained Raman spectra to find the Raman signatures corresponding to each type of the cervical tissue. In one embodiment, the Raman signatures comprise peaks and their corresponding wavelengths in the Raman spectra, wherein each peak and the corresponding wavelength correspond to a Raman band of a corresponding type of cervical tissue.

At step 130A, biochemical markers associated with cervical remodeling at each phase of pregnancy corresponding to the Raman signatures are identified.

In one embodiment, the biochemical markers are associated with collagen, lipids, nucleic acids and other proteins relevant to each phase of the cervical remodeling.

In one embodiment, the method further includes characterizing changes and trends of the biochemical markers over the course of pregnancy.

In one embodiment, the method further includes correlating the biochemical markers with clinical measures of pregnancy and outcomes.

In one embodiment, the method further includes comprising analyzing a longitudinal progression of cervical change using a generalized linear model (GLM) that satisfy $$Y=\beta X+\varepsilon$$

wherein Y is a vector containing the Raman signals, X is a matrix containing independent variables including gestational age, body mass index (BMI), and parity, $\beta$ is a vector containing weight coefficients of the independent variables, and $\varepsilon$ is a residual error in the GLM, wherein a linear least square regression is performed to choose the weight coefficients of $\beta$ such that $\varepsilon$ is minimized. In one embodiment, the method further includes correlating the Raman signals with measures of cervical length and Bishop score.

In one embodiment, the group of humans is with normal pregnancy, or with high risk pregnancy of PTB. In one embodiment, the method further includes correlating spectral changes from the group of humans with normal pregnancy and the group of humans with high risk pregnancy of PTB with clinical measures and biochemical markers so as to characterize their trends of changes in the group of humans with high risk pregnancy of PTB.

Figure 1B:
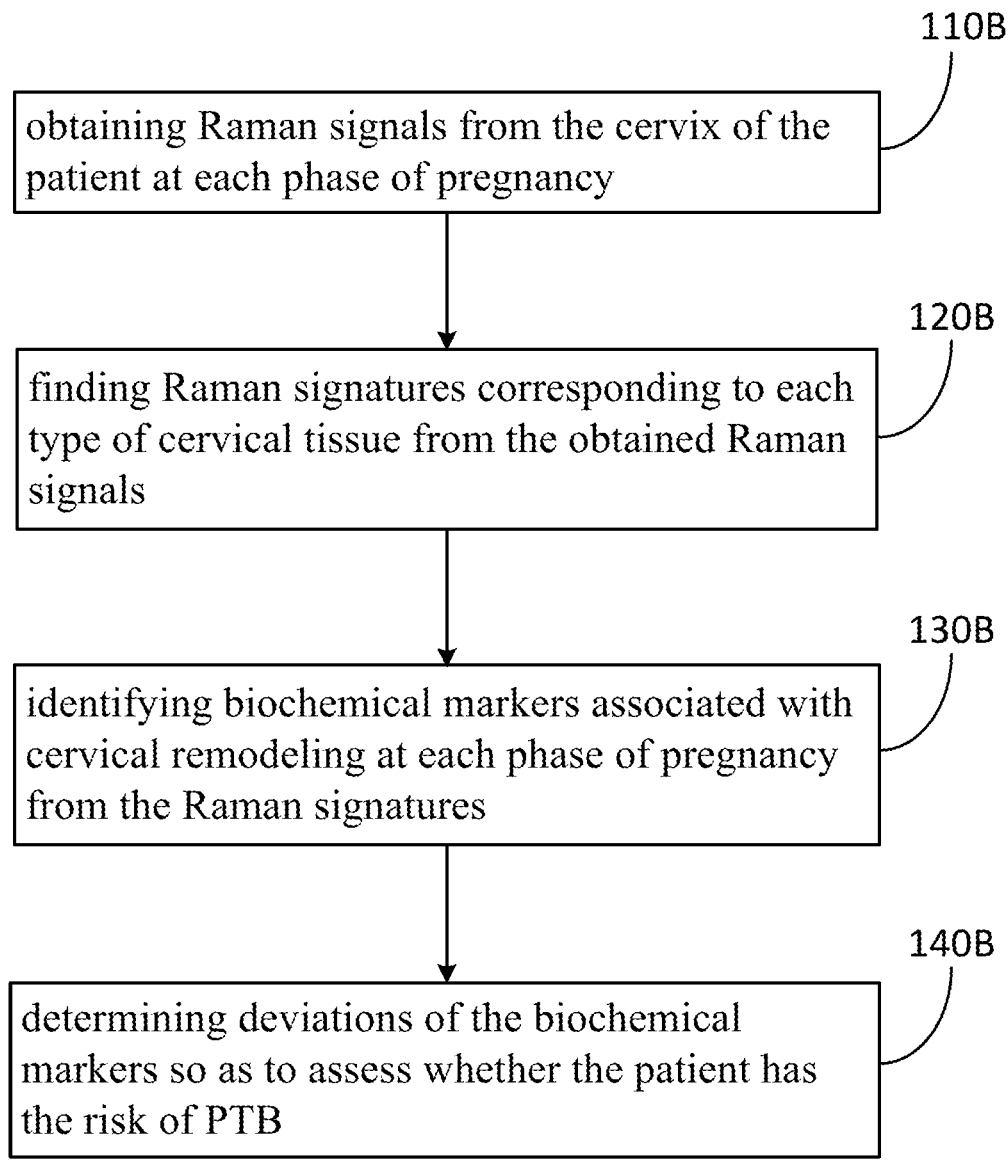
FIG. 1B shows a flowchart for assessing whether a patient with pregnancy has risk of PTB according to one embodiment of the invention.

Referring to FIG. 1B, a method for assessing whether a patient with pregnancy has risk of PTB is shown according to one embodiment of the invention. In this embodiment, the method includes the following steps.

At step 110B, Raman signals are obtained from the cervix of the patient at each phase of pregnancy.

In one embodiment, each of Raman signals is obtained by delivering a beam of light at a predetermined wavelength to the cervix to illuminate the cervix therewith; collecting light scattered from the cervix responsive to the illumination of the beam of light; and obtaining the Raman signal from the scattered light.

In one embodiment, the delivering and collecting is performed by a speculum-free optical probe.

In one embodiment, the predetermined wavelength comprises a wavelength in a near-infrared range.

At step 120B, Raman signatures corresponding to each type of cervical tissue are found from the obtained Raman signals.

In one embodiment, the Raman signals comprises Raman spectra, and wherein the finding step comprises processing the obtained Raman spectra to find the Raman signatures corresponding to each type of the cervical tissue.

In one embodiment, the Raman signatures comprise peaks and its corresponding wavelengths in the Raman spectra, wherein each peak and the corresponding wavelength correspond to a Raman band of a corresponding type of cervical tissue.

At step 130B, biochemical markers associated with cervical remodeling at each phase of pregnancy from the Raman signatures are identified.

In one embodiment, the biochemical markers are associated with collagen, lipids, nucleic acids and other proteins relevant to each phase of the cervical remodeling.

At step 140B, deviations of the biochemical markers so as to assess whether the patient has the risk of PTB are determined.

In one embodiment, the determining step comprises comparing the biochemical markers with a library of biochemical information that contains the biochemical markers associated with cervical remodeling over the course of pregnancy of humans to determine the deviations of the biochemical markers.

In yet another aspect, the invention relates to system for assessing whether a patient with pregnancy has risk of PTB.

In one embodiment, the system has an optical probe optically connected to a light source and configured to deliver a beam of light emitted from the light source to the cervix of the patient to illuminate the cervix therewith and to collect light scattered from the illuminated cervix; a detector optically coupled with the optical probe, for obtaining Raman singals from the collected scattered light; and a controller in communication with the detector and programmed to find Raman signatures corresponding to each type of cervical tissue from the obtained Raman signals; identify biochemical markers associated with cervical remodeling at each phase of pregnancy corresponding to the Raman signatures; and determine deviations of the biochemical markers so as to assess whether the patient has the risk of PTB.

In one embodiment, the light source comprises a laser or light emitting diodes (LEDs).

In one embodiment, the beam of light has a wavelength in a near-infrared range.

In one embodiment, the optical probe is speculum-free optical probe and has a working end, a housing, a delivery and collection means, a camera, and at least one rinse channel received in the housing, wherein the working end is operably positioned proximate to a surface of the cervix of the patient.

In one embodiment, the delivery and collection means comprises a plurality of fibers, wherein at least one fiber of the plurality of fibers is configured to deliver the beam of light emitted by the light source from the working end to the surface of the cervix so as to illuminated the cervix therewith, and the remaining fibers of the plurality of fibers are configured to collect from the working end light scattered from the illuminated cervix.

In one embodiment, the plurality of optical fibers is spatially arranged in a fiber array. In one embodiment, the at least one fiber for delivering the beam of light is positioned in a center of the fiber array, and the remaining fibers or collecting the scattered light are positioned in one or more rings surrounding the at least one fiber.

In one embodiment, the at least one rinse channel is adapted to apply saline or the like to clean tissue of the cervix.

In one embodiment, the working end of the optical probe is flat or rounded.

In one embodiment, the camera comprises a fiber camera, or an endoscopic camera.

In one embodiment, the optical probe further comprises a series of white light LEDs received in the housing and surrounding the camera.

In one embodiment, the optical probe further comprises an inflatable balloon placed at the working end for blocking environmental light.

In one embodiment, the detector comprises a spectrometer.

In one embodiment, the detector further comprises a CCD.

It should be noted that all or a part of the steps according to the embodiments of the present invention is implemented by hardware or a program instructing relevant hardware. Yet another aspect of the invention provides a non-transitory tangible computer-readable medium storing instructions which, when executed by one or more processors, cause the mobile or transportable device to perform the above method for automatically retuning a specific broadcast program from a first fixed location radio communication facility to a second fixed location radio communication facility. The computer executable instructions or program codes enable a computer or a similar computing system to complete various operations in the above disclosed method for privilege management. The storage medium/memory may include, but is not limited to, high-speed random access medium/ memory such as DRAM, SRAM, DDR RAM or other random access solid state memory devices, and non-volatile memory such as one or more magnetic disk storage devices, optical disk storage devices, flash memory devices, or other non-volatile solid state storage devices.

These and other aspects of the present invention are further described in the following section.

Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

According to the invention, RS is used to study pregnancy in humans so as to understand cervical remodeling during parturition in humans in vivo by characterizing the biochemical markers associated with each phase of pregnancy, e.g., the biochemical markers that occur during the four stages of cervical remodeling in healthy pregnancies, and identify Raman spectral markers indicative of early signs of PTB to predict risk, which determines how these changes deviate in high risk populations. The following studies conducted at the Vanderbilt One Hundred Oaks Women's Health Center and Vanderbilt University Medical Center are exemplary implementations of the invention.

Evaluation of Biochemical Markers Associated with Cervical Remodeling During Normal Human Pregnancies The normal changes that the pregnant cervix undergoes throughout pregnancy in preparation for labor as well as its return to the non-gravid state through the process of repair must be characterized and benchmarked against conventional clinical measures so that deviations from the normal are recognized. The goals are to understand cervical remodeling during normal human pregnancy in vivo and identify biochemical markers associated with each phase of the process. It should be noted that all four phases of the remodeling process in patients are studied, but in such a way as to seamlessly integrate with clinical care, using the fiber optic probe as disclosed above that minimizes patient discomfort.

In order to demonstrate the feasibility of obtaining Raman spectra from the pregnant cervix in vivo in humans and to obtain initial assessment of differing spectral features during cervical remodeling, two different pilot studies were conducted.

Softening and ripening phase: Thirty pregnant patients receiving prenatal care from Vanderbilt's Center for Women's Health were recruited (IRB 100544) for the ripening and softening phase of the study. Measurements were taken every six weeks in the first and second trimesters, and weekly in the third trimester. Raman bands attributed to phenylalanine (breathing mode), amide III (vibrational mode of C-N stretch and N-H bend in extracellular matrix (ECM) peptide backbone), CH2 attributed to lipids, and amide I (C=O stretch in ECM peptide backbone) all displayed a considerable amount of variability throughout pregnancy. The longitudinal progression of cervical change was analyzed by developing a generalized linear model (GLM) capable of incorporating results from Raman spectra. In order to make comparisons from the same patient throughout pregnancy, generalized estimating equations (GEE) were used. This method is an extension of GLM that clusters measurements obtained from the same patient [21, 22].

Figure 5A:
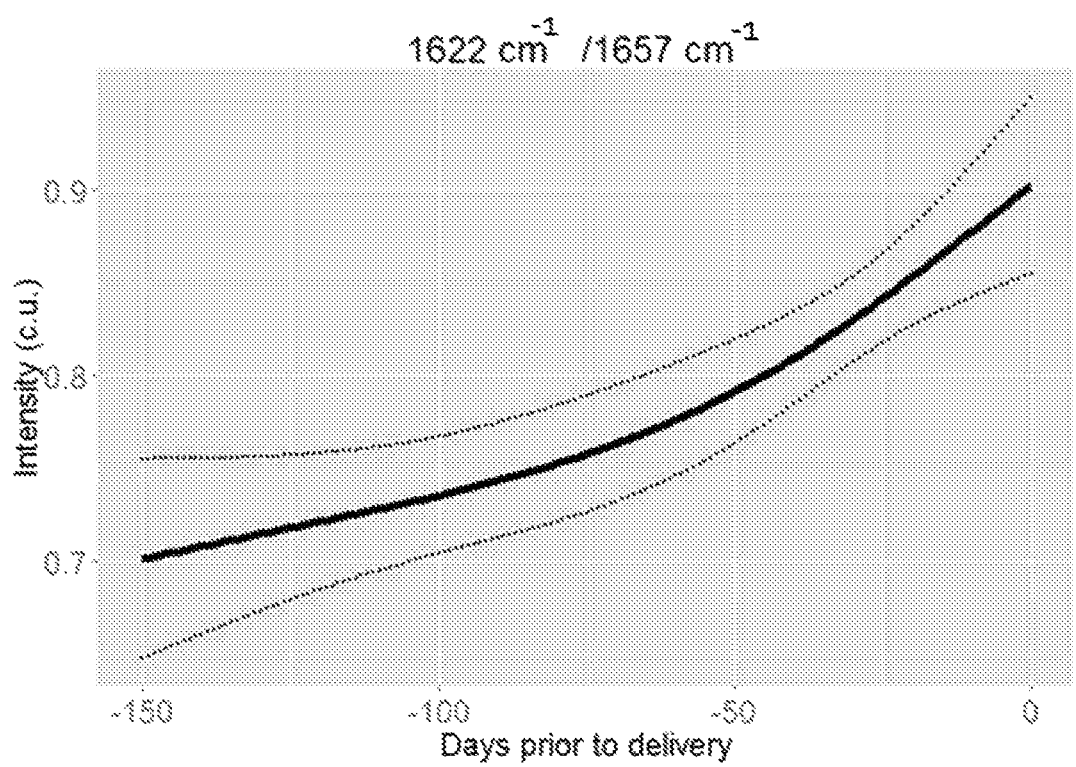
FIG. 5A shows a generalized linear model (GLM) of the Amide 1 peak broadening to peak intensity (1622 $cm^{-1}$/1657 $cm^{-1}$). Dotted lines indicate upper and lower bounds of the standard error.
Figure 5B:
FIG. 5B shows the GLM model of the phenylalanine to lipid ratio 1003 $cm^{-1}$/1440 $cm^{-1}$). Dotted lines indicate upper and lower bounds of the standard error.

FIG. 5A shows the ratio of ECM peak broadening to ECM peak intensity ($1622$ $cm^{-1}/1440$ $cm^{-1}$) which revealed a highly significant increase over the course of pregnancy ($p<0.001$). As the collagen matrix becomes more disorganized and less concentrated, the Amide I Raman peak located at $1657$ $cm^{-1}$ loses intensity and broadens, which has been readily detected in these patients as the cervix remodels. These changes began early in pregnancy and continued in a linear fashion until delivery, potentially revealing biochemical changes due to the softening phase of cervical remodeling. In contrast, FIG. 5B reveals an exponential increase in the phenylalanine to lipid peak ratio approximately six weeks prior to delivery. When these peaks were analyzed individually, the phenylalanine showed a gradual decrease whereas the lipid peak displayed a significant decrease in the last six weeks of pregnancy, effectively probing biochemical changes occurring on different time scales. It is possible that the changes observed in the last six weeks prior to delivery are part of the ripening phase of cervical remodeling.

Figure 6A:
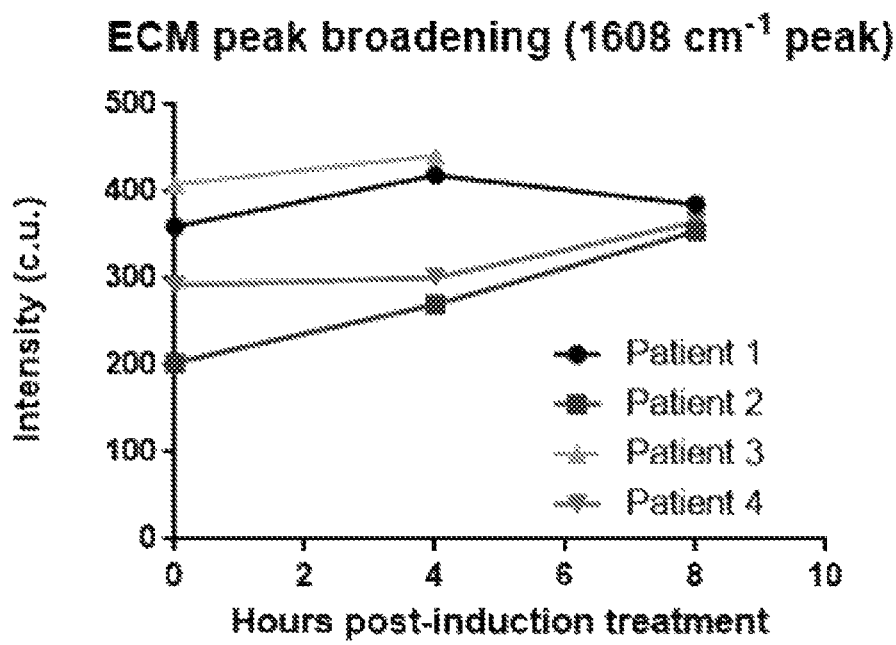
FIG. 6A shows peak broadening of the Amide I band which is sensitive to matrix organization was observed in all four labor induction patients as they progressed through their labor.
Figure 6B:
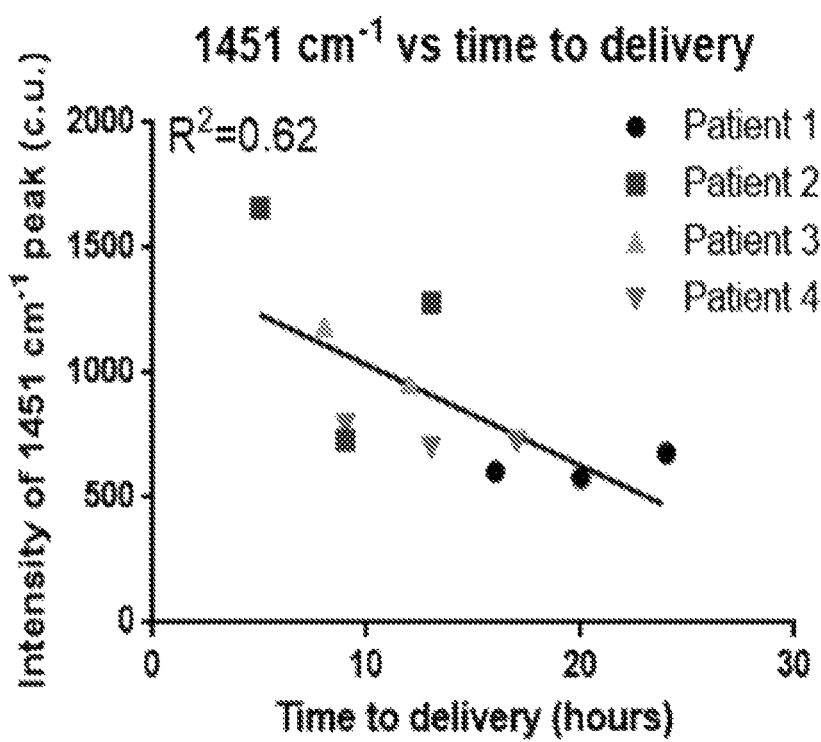
FIG. 6B shows a statistically significant correlation was observed between increasing lipid intensity (1440 $cm^{-1}$) and time until delivery.

Dilation phase: A separate cohort of patients undergoing labor by induction was recruited in this pilot study to assess the feasibility of acquiring RS from patients in labor. Preliminary results obtained from four women during labor are shown in FIGS. 6A-6B. An increase in Amide I broadening (FIG. 6A) similar to that in FIG. 5A was observed as labor progressed. In addition, a spike in lipids was observed prior to delivery (FIG. 6B). The origin of these lipid signals is currently unknown and warrants further study. While the preliminary results shown in FIGS. 6A-6B demonstrate the need to include this phase of cervical remodeling, the results also emphasize the need to follow the same patient through the entire cervical remodeling process due to the interpatient variability inherent in these patients. It is also likely that induced patients undergo an entirely unique ripening process compared with natural labor, and therefore this aim will track cervical changes throughout the entire pregnancy. Repair phase: The motivation for studying this phase of cervical modeling arises from the results of our animal study in which wild type mice with normal parturition were followed through the entire pregnancy cycle, as described and shown in FIGS. 4A-4C, which show that the cervical tissue spectral features as well as tensile measurements taken 1 day post-partum (P1) return to values observed in the non-gravid cervix (FIGS. 4B-4C). This quick rebound of the tissue state within 24 hours of delivery indicates that the cervix undergoes rapid changes in its biochemical state to return it to its pre-pregnancy state. This process presents an opportunity to track the reverse changes that occur to the cervix in a short time frame and allow us to improve our understanding of the cervix as it remodels during pregnancy.

In certain embodiments, the portable fiber optic probe-based Raman Spectroscopy system as disclosed above and shown in FIG. 8 is used to acquire Raman spectra from patients. The system includes a 785 nm diode laser coupled to a fiber optic probe. An imaging spectrograph coupled to an air-cooled back-illuminated, deep-depletion charge coupled device (CCD) camera, controlled with a computer collects the Raman signal. A custom dis-infectable fiber optic probe incorporating inline filtering within the tip of the probe to minimize interference from the components used in the probe itself is used in the study. Spectra are calibrated using standard protocols and processed for fluorescence subtraction and noise smoothing [56].

It is validated, through mathematical modeling using Monte Carlo simulation and thermal measurement that less than 1% of the laser light used to interrogate the tissue reaches 1 cm into the cervix and as such does not cause any harm to the mother or infant. Further, it is validated that no complications, injury, or pain was recorded in any of the patients as a result of participation in our preliminary study.

In certain embodiments, the speculum-free integrated Raman probe, as shown in FIG. 7A-7D, is used to excite the tissue and collect Raman data from the tissue in response to the excitation. In one embodiment shown in FIG. 7A, the speculum-free integrated Raman probe includes an optical probe including excitation and collection fibers (about 2.1 mm total in diameter), a fiber based camera (about 1 mm in diameter), a series of white light LEDs, and two saline rinse ports/channels (about 1 mm in diameter). The camera is used to visually guide the placement of the fiber probe under white light illumination. The saline flush channels are used to clear the cervix of any debris and mucous prior to placing the probe in contact with the tissue. The speculum-free integrated Raman probe is about 5 mm in diameter and disinfectable as required for routine care.

Prior to RS measurements, the vaginal canal and cervix are cleaned with a cotton swab and a digital exam is performed by a trained provider to locate the cervix. Next, the Raman probe is guided along the fingers of the provider under visual guidance with the built-in camera, which is used as needed by the provider-on-call. Once the Raman probe is in gentle contact with the ectocervix, the overhead lights are turned off and multiple Raman spectra are acquired. Since digital exams are routinely performed throughout the various phases of pregnancy as part of standard clinical practice and many levels of providers are trained to perform this exam, introducing the RS probe is integrated in the workflow effectively reducing the barriers to clinical translation of in vivo Raman spectroscopy.

Sample size estimation and patient recruitment: Pregnant patients that are expected to have an uncomplicated pregnancy, i.e., patients without known risk factors for PTB, and are receiving prenatal care from Vanderbilt's Center for Women's Health are recruited. IRB approval is obtained for normal pregnancies. The patient's provider determines if a patient is eligible to participate in the study based on strict inclusion/exclusion criteria, as well as their medical opinion. Informed written consent is obtained from each patient who is willing to participate in the study prior to performing any measurements. The patients can withdraw at any time by choice or by recommendation of their provider.

A standard two-tailed, two-sample student t-test was used to estimate the detectable difference (effect size) for the normal pregnancy study. The standard deviation of the lipid band at 1308 $cm^{-1}$ observed in preliminary Raman spectroscopy data from in vivo human cervix was used for the sample size estimation. Given a power of 80%, a level of significance of 5%, and a target sample size of 20 patients per group, it is determined that spectral differences of 0.22 calibrated units are detectable in this study.

Previous studies have shown that body mass index (BMI) and parity have an influence on the ability of RS to correctly characterize cervical spectra [57]. Further, race/ethnicity did not affect spectral classification. To account for the effect of parity, two groups of patients are recruited: 1) nulliparous patients and 2) patients with a prior pregnancy. Based on the 11.5% national average for preterm birth prevalence in 2015 and the retention falloff from the pilot study (25%), 31 patients are recruited in order to reach a target goal of 20 patients successfully reaching term in each group. In summary, 31 nulliparous patients, 31 patients with a prior pregnancy, and 20 patients undergoing routine gynecologic examination for testing of the speculum-free probe are recruited in this study.

Study protocol: Patient information such as age, parity, BMI, race, and obstetric and gynecological history are noted. For each patient at each visit, the vaginal canal and cervix are cleaned with a cotton swab and a digital exam is performed by a trained provider to locate the cervix. Next, the Raman probe is placed in gentle contact with the cervix, the overhead lights are turned off and Raman spectra are measured from 4 sites on the cervix at 12, 3, 6 and 9 o'clock positions using an integration time of 3 seconds per measurement. No tissue is removed as part of this study. All patient data are classified based on their gestation at the time of measurement. All measurements during the softening and ripening phase are made as part of routine clinical visits. Measurements are acquired every 4-6 weeks in the first and second trimester, and weekly in the third trimester. Once the patient goes to the Labor and Delivery unit at Vanderbilt, RS measurements are taken at the same time points that cervical exams are performed. Current practice at Vanderbilt is to perform cervical exams every four hours when the cervix is less than 6 cm dilated, and every two hours after the cervix is greater than 6 cm dilated. Once the membranes rupture, Raman measurements are no longer taken. Finally, postpartum measurements are taken immediately after delivery, prior to the patient being discharged, and at their 6-week post-partum visit scheduled with their provider. The various time points provide a trajectory of change, as the cervix softens, ripens, dilates, and repairs.

Two clinical measures are used along with the RS measurements to assess obstetric status: cervical length measured using transvaginal ultrasound and Bishop score obtained during digital exam. These clinical metrics are compared with Raman spectra, gestation length, and patient outcome.

Transvaginal ultrasound: From a transvaginal ultrasound (TVU) image, an experienced sonographer can calculate the length of the cervix. This method has been shown to be a valuable risk predictor for preterm labor [23], but can also be used as a simple measure of the degree of macroscale cervical remodeling. The reader can infer from the cervical length measured how "ripe" the cervix is based on structure. The method has a reported sensitivity of 56.5% and specificity of 71.1% for predicting spontaneous labor within the next 7 days. In developing a more complete picture of the events that lead to cervical dilation, TVU provides an important piece of information that can be used to correlate with measures of tissue biochemistry measured with Raman spectroscopy.

Bishop score: The Bishop score is used clinically to evaluate whether induction of labor is necessary; however, it has also been tested as a measure for predicting preterm labor. The score is based on 5 parameters that are determined by digital exam performed by the attending clinician. The parameters include cervical position, degree of cervical effacement (thinning), degree of dilation, degree of cervical softness, and fetal station. Clinically, the larger the Bishop score, the more likely labor is to start. However, the Bishop score is a subjective measure since the accuracy of each parameter is dependent on the level of experience and opinion of the provider. Thus, there is large variance in this measure across different providers. The method has a sensitivity of 45.2% and specificity of 76.3% for predicting spontaneous labor within 7 days. In this study, this score is utilized to evaluate the "clinical" state of the cervix at each time point and to correlate these measures to the Raman spectra obtained.

Data processing and analysis: The longitudinal progression of cervical change is analyzed by developing generalized linear models (GLM) capable of incorporating results from Raman spectra, as well as patient factors such as BMI and parity. General linear models follow the simple linear equation:

$$Y = \beta X + \varepsilon$$

where Y is a vector containing the dependent variable (in this case Raman spectra), X is a matrix containing independent variable(s) (gestational age, BMI, parity), β is a vector containing coefficients of the independent variables (weights), and ε is the residual error in the model. A linear least square regression method is then performed to choose β coefficients such that ε is minimized.

Figure 9:
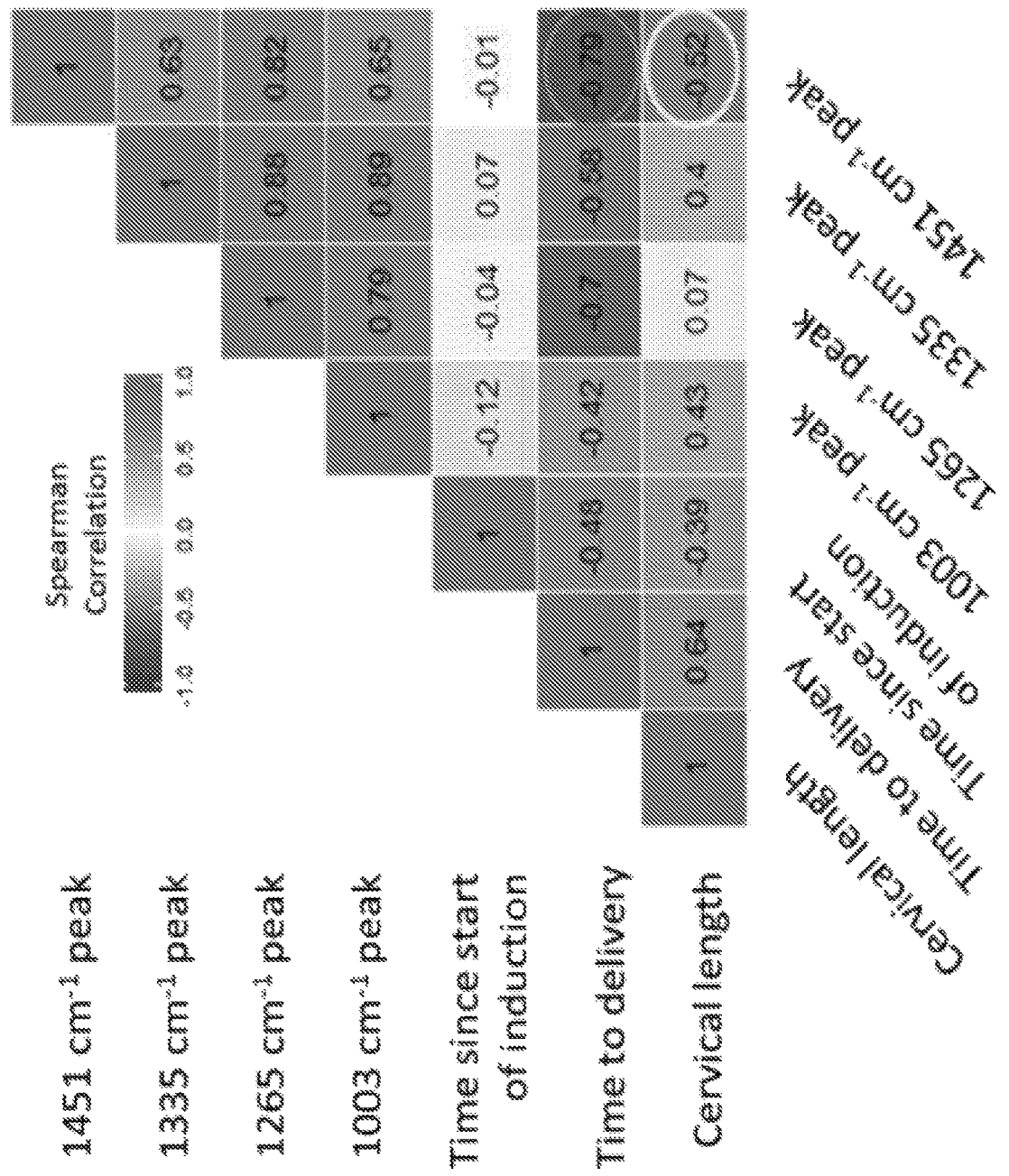
FIG. 9 shows Spearman correlation matrix including four Raman peaks and three clinical correlates. Strong positive correlations are shaded in red, while strong negative correlations are shaded in blue.

In order to make comparisons from the same patient throughout pregnancy, generalized estimating equations (GEE) are used. This method is an extension of GLM that clusters measurements obtained from the same patient [58]. This model helps to determine spectral changes that Raman spectroscopy is sensitive to. In addition, spectra are correlated with measures of cervical length and Bishop score. A Spearman correlation is performed for cervical length and Bishop score due to the continuous nature of these variables as demonstrated in preliminary results from laboring women shown in FIG. 9. In this preliminary analysis, three clinical measures, such as time since initiation of induction (hours), time to delivery (hours), and cervical length (cm), were compared to four Raman peaks (1451 $cm^{-1}$, 1335 $cm^{-1}$, 1265 $cm^{-1}$, and 1003 $cm^{-1}$). A significant correlation was observed between cervical length and the intensity of the 1451 $cm^{-1}$ peak (highlighted by the white circle), however the strongest correlation observed was between the increasing 1451 $cm^{-1}$ peak with the decreasing time until delivery (highlighted by the black circle), as shown also in FIG. 6B. For this and future analyses, outcomes are considered statistically significant if $p<0.05$.

According to embodiments of the invention, biochemical markers associated with collagen, lipids, nucleic acids and other proteins relevant to each phase of cervical remodeling are identified and their trends over the course of pregnancy are characterized. For example, in one embodiment, Raman signatures associated with extracellular matrix show exponential change over the course of pregnancy, starting with gradual differences in the first and second trimester and then accelerated rate of change in the third trimester and during labor. Since the Raman signals associated with softening, ripening, dilation, and repair phases are unique, one can have a solid understanding of the spectral changes that occur in uncomplicated pregnancies, and the rate in which they occur.

Identification of PTB Biochemical Markers in the Human Cervix from High Risk Pregnancy This study allows for a direct comparison of the observations and analysis obtained from patients with Raman spectra from patients known to be at a high risk for PTB and as such provides unique insight into the in vivo human pregnant cervix that has not previously been obtained. This study focuses on three high risk groups: 1) patients with a short cervix (measured less than 26 mm at 24 week ultrasound), 2) patients with prior history of preterm birth, and 3) patients with a body mass index greater than 40. These groups were chosen due to their prevalence yet incomplete understanding of their role in preterm birth. Spectral changes from normal and high risk patients are correlated with clinical measures and biochemical markers and their trends that change in patients with PTB are characterized. A statistical model is used to highlight deviations of these markers from the normal gestational process so that premature cervical remodeling can be understood and associated changes identified.

Our lab has used in vivo Raman spectroscopy to perform extensive work using mouse models of preterm birth and delayed parturition. This work is crucial to understanding the biochemical basis of Raman spectral signatures and has allowed us to characterize cervical change in a highly controlled manner. These studies provide insight into compromised cervical remodeling.

Preterm birth mouse models: the following two models of preterm birth were studied.

(1) Lipopolysaccharide (LPS) is an endotoxin found in the cell wall of Gram-negative bacteria, which elicits an inflammatory response in humans and animals. This is a well-established model of preterm labor that stimulates the onset of parturition within 8-12 hours. LPS was administered to wild type pregnant mice via intrauterine injection on day 15 (n=8) of gestation (CD-1 wildtype mice have a 19 day gestation with the presence of a post-copulatory plug on the morning after mating considered day 1).

(2) RU-486 (Mifepristone) is a progesterone receptor antagonist that is used clinically in women as an abortifacient, and the appropriate dose is known to stimulate the onset of labor in approximately 12 hours. RU-486 was administered via intraperitoneal injection on day 15 (n=8) to induce labor.

Figure 10A:
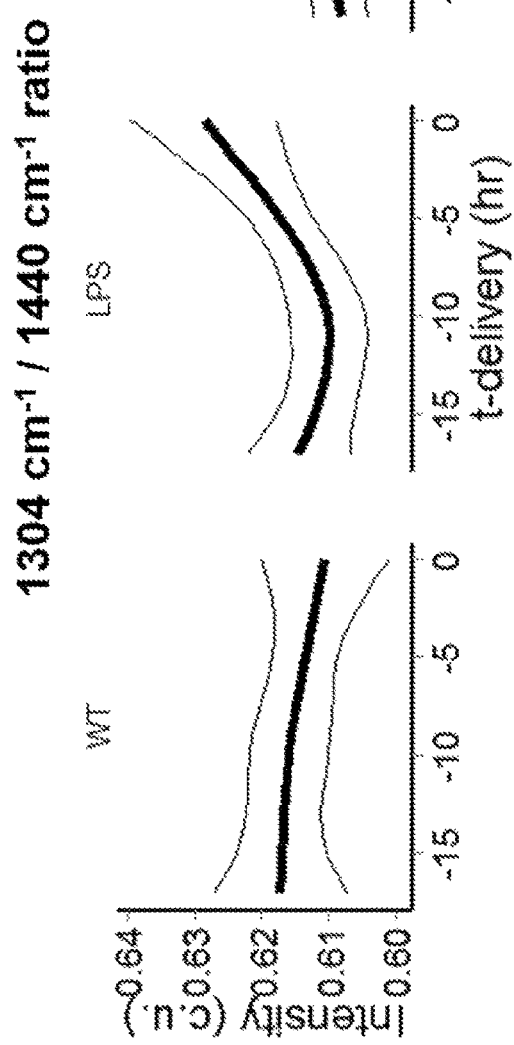
FIGS. 10A-10B respectively show modeled longitudinal trajectories of biochemical change in term wildtype and day 15 wild type-treated mice treated with LPS (FIG. 10A) and RU486 (FIG. 10A).
Figure 10B:
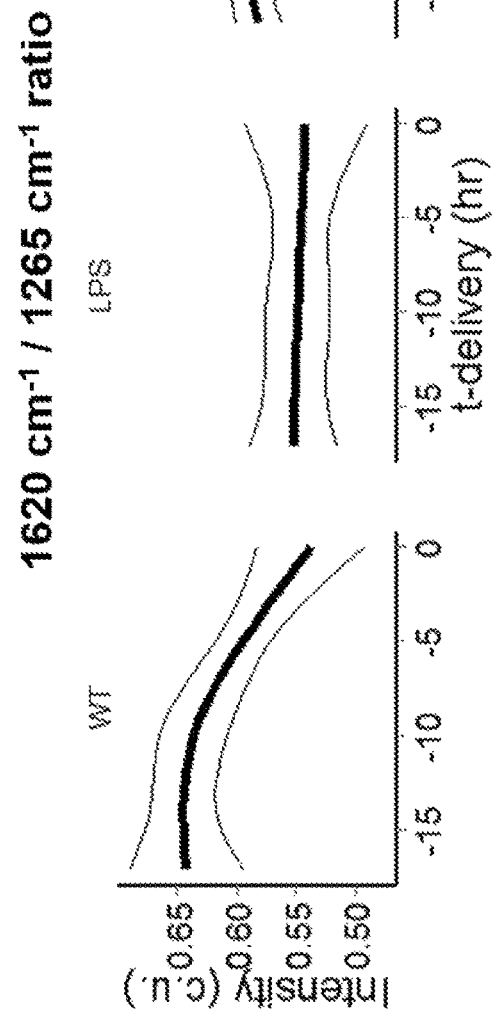

For both mouse models, Raman measurements were taken prior to treatment, and every two hours until delivery. Measurements from the wild type mice were initiated at noon on day 19 and obtained every 2 hours until delivery (average delivery time is midnight of day 19). Results from these studies are displayed in FIGS. 10A-10B, which reveal unique biochemical changes as the cervix remodels in preparation for delivery. The LPS-treated mice appear to follow an entirely different trajectory of change in remodeling than term and RU486-treated mice, which are more similar. The LPS mice display a significant increase in the DNA (1304 $cm^{-1}$) to lipid (1440 $cm^{-1}$) ratio prior to delivery compared to term and RU486-treated mice ($p<0.05$). Similarly, the Amide I peak broadening (ECM disorganization) (1620 $cm^{-1}$) to ECM (1265 $cm^{-1}$) ratio displays a significant decrease in term wild type and RU486-treated mice whereas the LPS treated mice remain unchanged ($p<0.05$). These results are supported by previous findings [58].

Delayed parturition mouse model: COX-1 (Ptgs1) null mice are missing a critical enzyme for prostaglandin production, a lipid known to be important for initiating labor in mice. These mice have delayed parturition by 1 to 2 days, and many pups do not survive. COX-1 null females have normal timing of implantation and normal litter size, making this a model with a truly prolonged gestational period and delay in parturition. FIG. 11A shows the trajectory of the DNA/ECM ratio (1304 $cm^{-1}$/1265 $cm^{-1}$), displaying a non-linear increase in the wild type compared to a slow linear increase in the COX-1 KO mice ($p<0.001$). The DNA signal shows a gradual increase over time, whereas the ECM proteins decline throughout pregnancy, resulting in a significant decrease in this ratio over gestation. The ECM to lipid ratio (1265 $cm^{-1}$/1440 $cm^{-1}$) displayed in FIG. 11B shows a non-linear decrease in the wild type mouse compared to a gradual linear decrease in the COX-1 KO mice, displaying a significant difference ($p<0.001$) in lipid (1440 $cm^{-1}$) and ECM signatures. In both of these plots, the wild type and the COX-1 KO mice begin with similar Raman spectral signatures, but beginning on day 12, the wild type mouse cervix starts to deviate in a non-linear fashion. Further, the COX-1 KO results never reach the level of the fully remodeled day 19 wild type cervix, even on gestation day 20. Ex vivo biomechanical testing revealed that the cervix of COX-1 KO mice were unable to dilate to the same extent as wild type on day 19 of pregnancy, validating the reduced degree of remodeling observed using in vivo Raman spectroscopy.

These studies demonstrate the ability of RS to reveal specific biochemical changes that can be associated with compromised pregnancies and as such provide the basis for the proposed work. These studies also emphasize the need for conducting studies in vivo in human patients to understand the trends in tissue biochemistry that are compromised in the various high risk patient populations.

Sample size estimation and patient recruitment: Pregnant patients receiving prenatal care from Vanderbilt's Center for Women's Health with the following risk factors are recruited: 1) 20 patients with a short cervix (measured less than 26 mm at 24 week ultrasound), 2) 20 patients with prior history of preterm birth, and 3) 20 patients with a BMI greater than 40. The patient's provider determines if a patient is eligible to participate in the study based on patient care and study protocol. Informed written consent is obtained from each patient who is willing to participate in the study prior to performing any measurements. The patients can withdraw at any time by choice or by recommendation of their provider. All issues related to scheduling and consent are managed by the research nurse budgeted in this proposal.

The same process used for calculating detectable difference (effect size) using a sample size of 20 patients yielded a detectable difference of 0.22 calibrated spectral units. Based on the 25% patient falloff rate experienced in our pilot study, 27 patients are recruited for each of the high risk categories, resulting in a total of 81 patients in this study. Patients experiencing preterm birth are not excluded from the sample size in the high risk categories.

Study protocol: patient information such as age, parity, BMI, race, and obstetric and gynecological history is noted. For each patient, the following protocol is used at each visit. The vaginal canal and cervix are cleaned with a cotton swab and a digital exam is performed by a trained provider to locate the cervix and the bishop score is noted. Next, the Raman probe is guided along the fingers during digital exam and placed on the ectocervix with visual guidance. Once the probe is in gentle contact with the ectocervix, the overhead lights are turned off and the Raman measurements are performed using the instrument and probe. All patient data are classified based on their gestation at the time of measurement. Measurements are acquired every 4-6 weeks in the first and second trimester, and weekly in the third trimester. Once the patient goes to the Labor and Delivery unit at Vanderbilt, measurements are taken at the same time points that cervical exams are performed. Current practice at Vanderbilt is to perform cervical exams every four hours when the cervix is less than 6 cm dilated, and every two hours after the cervix is greater than 6 cm dilated. Once the membranes rupture or the cervix is less than 1 cm in length as measured by transvaginal ultrasound by a trained sonographer, Raman measurements are no longer taken. Finally, post-partum measurements are taken immediately after delivery, prior to the patient being discharged, and at their 6-week post-partum visit scheduled with their provider. The acquired Raman spectral signatures are compared to cervical length and the Bishop Score. No tissue is removed as part of this study.

Data processing and analysis: the longitudinal progression of cervical change is analyzed by developing GEE, an extension of GLM that clusters measurements from the same patient across the analysis. This model is capable of incorporating results from Raman spectra, as well as patient factors such as high risk category, BMI and parity. A Spearman correlation is performed for cervical length and Bishop score due to the continuous nature of these variables. Outcomes are considered statistically significant if $p<0.05$.

Raman trends associated with softening, ripening, dilation, and repair phases are unique and differ in each of the three high risk groups as compared to normal pregnancies. Furthermore, the biochemical state of the cervix in each of these high risk categories has their own remodeling profiles that are predictive of patient outcome. These differences manifest as an accelerated rate of change that otherwise appears similar to normal cervical remodeling; however, it is likely that entirely different spectral signatures may be identified. Accordingly, it is found how the biochemical markers associated with cervical remodeling, particularly in those who ultimately deliver preterm, differ from those in term, normal pregnancies.

Maternal health providers all over the world are in need of accurate methods to recognize patients at risk of preterm birth. Understanding cervical remodeling opens the door to detecting premature cervical remodeling as a promising strategy to identify such patients. Our preliminary work in pregnant patients and mice demonstrates the ability of in vivo Raman measurements to provide important biochemical information about cervical remodeling. The knowledge gained from these studies facilitate the collective understanding of the biochemical processes that occur in the cervix in normal and high risk pregnancies, and aid in global efforts to close the gap of understanding and ultimately reduce incidence, morbidity, and mortality caused by preterm birth.

Briefly, among other things, the innovations of the invention are the application of RS for the study of a process, pregnancy, and its concomitant normal physiological and structural changes; the ability to obtain detailed biochemical information in vivo in humans related to the pregnancy process; correlations between these biochemical markers, clinical measures of pregnancy and patient outcomes, which lead to a better understanding of normal pregnancy; identification of deviations of these biochemical markers when the pregnancy process is complicated such as in preterm birth; and the investigation of all phases of cervical remodeling include repair, i.e., the post-partum cervix. While much attention has been given to understanding the changes associated with pregnancy leading up to parturition, little work has focused on the recovery process following delivery; significant insight may be gleaned from the process by which the cervix rebounds immediately after dilation and delivery. Furthermore, another innovation of the invention is directly targeted for implementation of RS within the population under study so that in vivo measurements may be made with minimal interference to patient care and little or no discomfort to the patient.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LISTING OF REFERENCES

[1]. Blencowe H, Cousens S, Chou D, Oestergaard M, Say L, Moller A-B, Kinney M, Lawn J. Born Too Soon: The global epidemiology of 15 million preterm births. Reproductive Health. 2013; 10 (Suppl 1): 1. PubMed PMID: 1463933756; 18811758.

[2]. Behrman R E, Butler A S. Preterm birth: causes, consequences, and prevention: National Academies Press; 2006.

[3]. Menon R. Spontaneous preterm birth, a clinical dilemma: etiologic, pathophysiologic and genetic heterogeneities and racial disparity. Acta Obstet Gynecol Scand. 2008; 87(6): 590-600. Epub 2008 Jun. 24. doi: 10.1080/00016340802005126. PubMed PMID: 18568457.

[4]. Ruiz R J, Fullerton J, Dudley D J. The interrelationship of maternal stress, endocrine factors and inflammation on gestational length. Obstetrical & gynecological survey. 2003; 58(6): 415-28.

[5]. Robinson J N, Regan J A, Norwitz E R, editors. The epidemiology of preterm labor. Seminars in Perinatology; 2001: Elsevier.

[6]. Macdonald P C, Gant N F, Leveno K J, Gilstrap L C, Hankins G, Clark S L. Williams Obstetrics 20th Edition: Appleton & Lange; 1996.

[7]. Hacker N F, Gambone J C, Hobel C J. Hacker & Moore's Essentials of Obstetrics and Gynecology: Saunders; 2009.

[8]. Jams J D. Prediction and early detection of preterm labor. Obstet Gynecol. 2003; 101(2): 402-12. PubMed PMID: 12576267.

[9]. Catalano P M, Ashikaga T, Mann L I. Cervical change and uterine activity as predictors of preterm delivery. American journal of perinatology. 1989; 6(02): 185-90.

[10]. Lee H J, Park T C, Norwitz E R. Management of pregnancies with cervical shortening: a very short cervix is a very big problem. Reviews in Obstetrics and Gynecology. 2009; 2(2): 107.

[11]. Moroz L A, Simhan H N. Rate of sonographic cervical shortening and the risk of spontaneous preterm birth. American Journal of Obstetrics and Gynecology. 2012; 206(3): 234 .e1-.e5.

[12]. Okitsu O, Mimura T, Nakayama T, Aono T. Early prediction of preterm delivery by transvaginal ultrasonography. Ultrasound in Obstetrics & Gynecology. 1992; 2(6): 402-9.

[13]. Ludmir J, Sehdev H M. Anatomy and physiology of the uterine cervix. Clinical Obstetrics and Gynecology. 2000; 43(3): 433-9. Epub 2000 Aug. 19. PubMed PMID: 10949747.

[14]. Aspden R M. Collagen organisation in the cervix and its relation to mechanical function. Coll Relat Res. 1988; 8(2): 103-12. PubMed PMID: 3378391.

[15]. Word R A, Li X-H, Hnat M, Carrick K, editors. Dynamics of cervical remodeling during pregnancy and parturition: mechanisms and current concepts. Seminars in reproductive medicine; 2007.

[16]. Leppert P C. Anatomy and physiology of cervical ripening. Clinical Obstetrics and Gynecology. 1995; 38(2): 267-79.

[17]. Osmers R, Rath W, Adelmann-Grill B, Fittkow C, Kuloczik M, Szeverenyi M, Tschesche H, Kuhn W. Origin of cervical collagenase during parturition. American Journal of Obstetrics and Gynecology. 1992; 166(5): 1455-60.

[18]. Myers K M, Paskaleva A, House M, Socrate S. Mechanical and biochemical properties of human cervical tissue. Acta Biomaterialia. 2008; 4(1): 104-16.

[19]. House M, Kaplan D L, Socrate S. Relationships Between Mechanical Properties and Extracellular Matrix Constituents of the Cervical Stroma During Pregnancy. Seminars in Perinatology. 2009; 33(5): 300-7. doi: 10.1053/j.semperi.2009.06.002.

[20]. Akins M L, Luby-Phelps K, Bank R A, Mahendroo M. Cervical softening during pregnancy: regulated changes in collagen cross-linking and composition of matricellular proteins in the mouse. Biology of Reproduction. 2011; 84(5): 1053-62.

[21]. Rechberger T, Uldbjerg N, Oxlund H. Connective tissue changes in the cervix during normal pregnancy and pregnancy complicated by cervical incompetence. Obstet Gynecol. 1988; 71(4): 563-7. Epub 1988 Apr. 1. PubMed PMID: 3353047.

[22]. Myers K M, Socrate S, Paskaleva A, House M. A study of the anisotropy and tension/compression behavior of human cervical tissue. Journal of Biomechanical Engineering. 2010; 132(2): 021003-.

[23]. Myers K, Socrate S, Tzeranis D, House M. Changes in the biochemical constituents and morphologic appearance of the human cervical stroma during pregnancy. European Journal of Obstetrics & Gynecology and Reproductive Biology. 2009; 144: S82-S9.

[24]. Feltovich H, Hall T J, Berghella V. Beyond cervical length: emerging technologies for assessing the pregnant cervix. American Journal of Obstetrics and Gynecology. 2012; 207(5): 345-54.

[25]. Jokhi R, Brown B, Anumba D. The role of cervical Electrical Impedance Spectroscopy in the prediction of the course and outcome of induced labour. BMC Pregnancy and Childbirth. 2009; 9(1): 40.

[26]. McFarlin B, Bigelow T, Laybed Y, O'Brien W, Oelze M, Abramowicz J. Ultrasonic attenuation estimation of the pregnant cervix: a preliminary report. Ultrasound in Obstetrics & Gynecology. 2010; 36(2): 218-25.

[27]. Feltovich H, Nam K, Hall T J. Quantitative ultrasound assessment of cervical microstructure. ULTRASONIC IMAGING. 2010; 32(3): 131-42.

[28]. Swiatkowska-Freund M, Preis K. Elastography of the uterine cervix: implications for success of induction of labor. Ultrasound in Obstetrics & Gynecology. 2011; 38(1): 52-6.

[29]. Badir S, Mazza E, Zimmermann R, Bajka M. Cervical softening occurs early in pregnancy: characterization of cervical stiffness in 100 healthy women using the aspiration technique. Prenatal diagnosis. 2013: 1-6.

[30]. Anthony G S, Walker R G, Robins J B, Cameron A D, Calder A A. Management of cervical weakness based on the measurement of cervical resistance index. European Journal of Obstetrics & Gynecology and Reproductive Biology. 2007; 134(2): 174-8.

[31]. Myers K, Ateshian G A. Interstitial growth and remodeling of biological tissues: Tissue composition as state variables. Journal of the mechanical behavior of biomedical materials. 2013.

[32]. Maul H, Saade G, Garfield R E. Prediction of term and preterm parturition and treatment monitoring by measurement of cervical cross-linked collagen using light-induced fluorescence. Acta Obstetricia et Gynecologica Scandinavica. 2005; 84(6): 534-6. doi: 10.1111/j.0001-6349.2005.00806.x.

[33]. Maul H, Olson G, Fittkow C T, Saade G R, Garfield R E. Cervical light-induced fluorescence in humans decreases throughout gestation and before delivery: preliminary observations. American Journal of Obstetrics and Gynecology. 2003; 188(2): 537-41.

[34]. Schlembach D, MacKay L, Shi L, Maner W L, Garfield R E, Maul H. Cervical ripening and insufficiency: From biochemical and molecular studies to in vivo clinical examination. European Journal of Obstetrics & Gynecology and Reproductive Biology. 2009; 144, Supplement 1(0): S70-S6. doi: 10.1016/j.ejogrb.2009.02.036.

[35]. Zhang Y, Akins M L, Murari K, Xi J, Li M J, Luby-Phelps K, Mahendroo M, Li X. A compact fiber-optic SHG scanning endomicroscope and its application to visualize cervical remodeling during pregnancy. Proceedings of the National Academy of Sciences. 2012; 109(32): 12878-83.

[36]. Reusch L M, Feltovich H, Carlson L C, Hall G, Campagnola P J, Eliceiri K W, Hall T J. Nonlinear optical microscopy and ultrasound imaging of human cervical structure. Journal of Biomedical Optics. 2013; 18(3): 031110-.

[37]. Baños A, Wolf M, Grawe C, Stahel M, Haensse D, Fink D, Hornung R. Frequency domain near-infrared spectroscopy of the uterine cervix during cervical ripening. Lasers in Surgery and Medicine. 2007; 39(8): 641-6.

[38]. Hornung R, Spichtig S, Baños A, Stahel M, Zimmermann R, Wolf M. Frequency-domain near-infrared spectroscopy of the uterine cervix during regular pregnancies.

[39]. Robichaux-Viehoever A, Kanter E, Shappell H, Billheimer D, Jones III H, Mahadevan-Jansen A. Characterization of Raman Spectra Measured<i> in Vivo</i> for the Detection of Cervical Dysplasia. Applied Spectroscopy. 2007; 61(9): 986-93.

[40]. Crow P, Molckovsky A, Stone N, Uff J, Wilson B, Wongkeesong L-M. Assessment of fiberoptic near-infrared Raman spectroscopy for diagnosis of bladder and prostate cancer. Urology. 2005; 65(6): 1126-30.

[41]. Grimbergen M, van Swol C, van Moorselaar R, Uff J, Mahadevan-Jansen A, Stone N. Raman spectroscopy of bladder tissue in the presence of 5-aminolevulinic acid. Journal of Photochemistry and Photobiology B: Biology. 2009; 95(3): 170-6.

[42]. Barr H, Kendall C, Bazant-Hegemark F, Moayyedi P, Shetty G, Stone N. Endoscopic Screening and Surveillance for Barrett's Esophagus—Clinical Implications. Medscape General Medicine. 2006; 8(2): 88.

[43]. Shetty G, Kendall C, Shepherd N, Stone N, Barr H. Raman spectroscopy: elucidation of biochemical changes in carcinogenesis of oesophagus. British journal of cancer. 2006; 94(10): 1460-4.

[44]. Chrit L, Bastien P, Sockalingum G, Batisse D, Leroy F, Manfait M, Hadjur C. An in vivo randomized study of human skin moisturization by a new confocal Raman fiber-optic microprobe: assessment of a glycerol-based hydration cream. Skin pharmacology and physiology. 2006; 19(4): 207-15.

[45]. Sigurdsson S, Philipsen P A, Hansen L K, Larsen J, Gniadecka M, Wulf H-C. Detection of skin cancer by classification of Raman spectra. Biomedical Engineering, IEEE Transactions on. 2004; 51(10): 1784-93.

[46]. Haka A S, Shafer-Peltier K E, Fitzmaurice M, Crowe J, Dasari R R, Feld M S. Diagnosing breast cancer by using Raman spectroscopy. Proceedings of the National Academy of Sciences of the United States of America. 2005; 102(35): 12371-6.

[47]. Bergholt M S, Zheng W, Lin K, Ho K Y, Teh M, Yeoh K G, So J B Y, Huang Z. Characterizing variability in in vivo Raman spectra of different anatomical locations in the upper gastrointestinal tract toward cancer detection. Journal of Biomedical Optics. 2011; 16(3): 037003-10.

[48]. Kanter E M, Majumder S, Kanter G J, Woeste E M, Mahadevan-Jansen A. Effect of hormonal variation on Raman spectra for cervical disease detection. American Journal of Obstetrics and Gynecology. 2009; 200(5):512.e1-.e5.

[49]. Morris M D, Mandair G S. Raman assessment of bone quality. Clinical Orthopaedics and Related Research®. 2011; 469:2160-9.

[50]. Mahadevan-Jansen A, Mitchell M F, Ramanujam N, Utzinger U, Richards-Kortum R. Development of a Fiber Optic Probe to Measure NIR Raman Spectra of Cervical Tissue In Vivo. Photochemistry and Photobiology. 1998; 68(3): 427-31. doi: 10.1111/j.1751-1097.1998.tb09703.x.

[51]. Mahadevan-Jansen A, Richards-Kortum R R. Raman spectroscopy for the detection of cancers and precancers. Journal of Biomedical Optics. 1996; 1(1): 31-70.

[52]. Kanter E M, Majumder S, Vargis E, Robichaux-Viehoever A, Kanter G J, Shappell H, Jones Iii H W, Mahadevan-Jansen A. Multiclass discrimination of cervical precancers using Raman spectroscopy. Journal of Raman Spectroscopy. 2009; 40(2): 205-11. doi: 10.1002/jrs.2108.

[53]. Kanter E M, Vargis E, Majumder S, Keller M D, Woeste E, Rao G G, Mahadevan-Jansen A. Application of Raman spectroscopy for cervical dysplasia diagnosis. Journal of Biophotonics. 2009; 2 (1-2): 81-90. doi: 10.1002/jbio.200910001.

[54]. Vargis E, Byrd T, Logan Q, Khabele D, Mahadevan-Jansen A. Sensitivity of Raman spectroscopy to normal patient variability. Journal of Biomedical Optics. 2011; 16(11): 117004-.doi: 10.1117/1.3646210.

[55]. Vargis E, Brown N, Williams K, Al-Hendy A, Paria B, Reese J, Mahadevan-Jansen A. Detecting Biochemical Changes in the Rodent Cervix During Pregnancy Using Raman Spectroscopy. Annals of Biomedical Engineering. 2012; 40(8): 1814-24. doi: 10.1007/s10439-012-0541-4.

[56]. Lieber C A, Mahadevan-Jansen A. Automated method for subtraction of fluorescence from biological Raman spectra. Appl Spectrosc. 2003; 57(11): 1363-7. Epub 2003 Dec. 9. PubMed PMID: 14658149.

[57]. Vargis E, Byrd T, Logan Q, Khabele D, Mahadevan-Jansen A. Sensitivity of Raman spectroscopy to normal patient variability. Journal of Biomedical Optics. 2011; 16(11): 117004-1170049.

[58]. Holt R, Timmons B C, Akgul Y, Akins M L, Mahendroo M. The molecular mechanisms of cervical ripening differ between term and preterm birth. Endocrinology. 2011; 152(3): 1036-46.

What is claimed is:

1. A method for identification of biochemical markers associated with cervical remodeling over the course of pregnancy of humans, comprising:
   obtaining, with a detector, Raman signals from the cervix of each of pregnant humans at each phase of pregnancy;
   finding, by a controller in communication with the detector, Raman signatures corresponding to each type of cervical tissue from the obtained Raman signals; and
   identifying, by the controller, biochemical markers associated with cervical remodeling at each phase of pregnancy corresponding to the Raman signatures.

2. The method of claim 1, wherein each of Raman signals is obtained by delivering a beam of light at a predetermined wavelength to the cervix to illuminate the cervix therewith;

collecting light scattered from the cervix responsive to the illumination of the beam of light; and obtaining the Raman signal from the scattered light.

3. The method of claim 2, wherein the delivering and collecting is performed by a speculum-free optical probe.

4. The method of claim 2, wherein the predetermined wavelength comprises a wavelength in a near-infrared range.

5. The method of claim 1, wherein the Raman signals comprises Raman spectra, and wherein the finding step comprises processing the obtained Raman spectra to find the Raman signatures corresponding to each type of the cervical tissue.

6. The method of claim 5, wherein the Raman signatures comprise peaks and their corresponding wavelengths in the Raman spectra, wherein each peak and the corresponding wavelength correspond to a Raman band of a corresponding type of cervical tissue.

7. The method of claim 1, further comprising characterizing changes and trends of the biochemical markers over the course of pregnancy.

8. The method of claim 1, further comprising correlating the biochemical markers with clinical measures of pregnancy and outcomes.

9. The method of claim 1, wherein the biochemical markers are associated with collagen, lipids, nucleic acids and other proteins relevant to each phase of the cervical remodeling.

10. The method of claim 1, further comprising analyzing a longitudinal progression of cervical change using a generalized linear model (GLM) that satisfy $$Y=\beta X+\varepsilon$$

wherein Y is a vector containing the Raman signals, X is a matrix containing independent variables including gestational age, body mass index (BMI), and parity, β is a vector containing weight coefficients of the independent variables, and ε is a residual error in the GLM, wherein a linear least square regression is performed to choose the weight coefficients of β such that ε is minimized.

11. The method of claim 1, further comprising correlating the Raman signals with measures of cervical length and Bishop score.

12. The method of claim 1, wherein the group of humans is with normal pregnancy, or with high risk pregnancy of preterm birth (PTB).

13. The method of claim 12, further comprising correlating spectral changes from the group of humans with normal pregnancy and the group of humans with high risk pregnancy of PTB with clinical measures and biochemical markers so as to characterize their trends of changes in the group of humans with high risk pregnancy of PTB.

14. The method of claim 1, wherein the biochemical markers are associated with collagen, lipids, nucleic acids and other proteins relevant to each phase of the cervical remodeling.

15. A method for assessing whether a patient with pregnancy has risk of preterm birth (PTB), comprising:

obtaining, by a detector, Raman signals from the cervix of the patient at each phase of pregnancy;

finding, by a controller in communication with the detector, Raman signatures corresponding to each type of cervical tissue from the obtained Raman signals;

identifying, by the controller, biochemical markers associated with cervical remodeling at each phase of pregnancy from the Raman signatures; and determining, by the controller, deviations of the biochemical markers so as to assess whether the patient has the risk of PTB.

16. The method of claim 15, wherein each of Raman signals is obtained by delivering a beam of light at a predetermined wavelength to the cervix to illuminate the cervix therewith;

collecting light scattered from the cervix responsive to the illumination of the beam of light; and obtaining the Raman signal from the scattered light.

17. The method of claim 16, wherein the delivering and collecting is performed by a speculum-free optical probe.

18. The method of claim 16, wherein the predetermined wavelength comprises a wavelength in a near-infrared range.

19. The method of claim 15, wherein the Raman signals comprises Raman spectra, and wherein the finding step comprises processing the obtained Raman spectra to find the Raman signatures corresponding to each type of the cervical tissue.

20. The method of claim 19, wherein the Raman signatures comprise peaks and its corresponding wavelengths in the Raman spectra, wherein each peak and the corresponding wavelength correspond to a Raman band of a corresponding type of cervical tissue.

21. The method of claim 15, wherein the determining step comprises comparing the biochemical markers with a library of biochemical information that contains the biochemical markers associated with cervical remodeling over the course of pregnancy of humans to determine the deviations of the biochemical markers.

22. A system for assessing whether a patient with pregnancy has risk of preterm birth (PTB), comprising:

an optical probe optically connected to a light source and configured to deliver a beam of light emitted from the light source to the cervix of the patient to illuminate the cervix therewith and to collect light scattered from the illuminated cervix;

a detector optically coupled with the optical probe, for obtaining Raman signals from the collected scattered light; and a controller in communication with the detector and programmed to find Raman signatures corresponding to each type of cervical tissue from the obtained Raman signals; identify biochemical markers associated with cervical remodeling at each phase of pregnancy corresponding to the Raman signatures; and determine deviations of the biochemical markers so as to assess whether the patient has the risk of PTB.

23. The system of claim 22, wherein the light source comprises a laser or light emitting diodes (LEDs).

24. The system of claim 23, wherein the beam of light has a wavelength in a near-infrared range.

25. The system of claim 22, wherein the optical probe is speculum-free optical probe and has a working end, a housing, a delivery and collection means, a camera, and at least one rinse channel received in the housing, wherein the working end is operably positioned proximate to a surface of the cervix of the patient.

26. The system of claim 25, wherein the delivery and collection means comprises a plurality of fibers, wherein at least one fiber of the plurality of fibers is configured to deliver the beam of light emitted by the light source from the working end to the surface of the cervix so as to illuminated the cervix therewith, and the remaining fibers of the plurality of fibers are configured to collect from the working end light scattered from the illuminated cervix.

27. The system of claim 26, wherein the plurality of optical fibers is spatially arranged in a fiber array.

28. The system of claim 27, wherein the at least one fiber for delivering the beam of light is positioned in a center of the fiber array, and the remaining fibers or collecting the scattered light are positioned in one or more rings surrounding the at least one fiber.

29. The system of claim 25, wherein the at least one rinse channel is adapted to apply saline or the like to clean tissue of the cervix.

30. The system of claim 25, wherein the working end of the optical probe is flat or rounded.

31. The system of claim 25, wherein the camera comprises a fiber camera, or an endoscopic camera.

32. The system of claim 25, wherein the optical probe further comprises a series of white light LEDs received in the housing and surrounding the camera.

33. The system of claim 25, wherein the optical probe further comprises an inflatable balloon placed at the working end for blocking environmental light.

34. The system of claim 33, wherein the detector further comprises a charge-coupled device (CCD).

35. The system of claim 25, wherein the detector comprises a spectrometer.

36. A speculum-free optical probe, comprising:
a working end, a housing, a delivery and collection means, a camera, and at least one rinse channel received in the housing, wherein the working end is operably positioned proximate to target tissue; and
a series of white light LEDs received in the housing and surrounding the camera.

37. The speculum-free optical probe of claim 36, wherein the delivery and collection means comprises a plurality of fibers, wherein at least one fiber of the plurality of fibers is configured to deliver the beam of light emitted by the light source from the working end to the target tissue so as to illuminated the target tissue therewith, and the remaining fibers of the plurality of fibers are configured to collect from the working end light scattered from the illuminated target tissue.

38. The speculum-free optical probe of claim 37, wherein the plurality of optical fibers is spatially arranged in a fiber array.

39. The speculum-free optical probe of claim 37, wherein the at least one fiber for delivering the beam of light is positioned in a center of the fiber array, and the remaining fibers or collecting the scattered light are positioned in one or more rings surrounding the at least one fiber.

40. The speculum-free optical probe of claim 36, wherein the at least one rinse channel is adapted to apply saline or the like to clean the target tissue.

41. The speculum-free optical probe of claim 36, wherein the working end of the optical probe is flat or rounded.

42. The speculum-free optical probe of claim 36, wherein the camera comprises a fiber camera, or an endoscopic camera.

43. The speculum-free optical probe of claim 36, further comprising an inflatable balloon placed at the working end for blocking environmental light.

* * * * *